United States Patent
Ramadass et al.

(10) Patent No.: US 11,535,893 B2
(45) Date of Patent: Dec. 27, 2022

(54) TYPING METHOD

(71) Applicant: Oxford BioDynamics PLC, Oxford (GB)

(72) Inventors: Aroul Selvam Ramadass, Oxford (GB); Ewan Hunter, Oxford (GB); Alexandre Akoulitchev, Oxford (GB)

(73) Assignee: Oxford BioDynamics PLC, Oxford (GB)

( * ) Notice: Subject to any disclaimer, the term of this patent is extended or adjusted under 35 U.S.C. 154(b) by 164 days.

(21) Appl. No.: 16/446,255

(22) Filed: Jun. 19, 2019

(65) Prior Publication Data

US 2019/0309367 A1 Oct. 10, 2019

Related U.S. Application Data

(63) Continuation of application No. PCT/GB2016/054076, filed on Dec. 23, 2016.

(51) Int. Cl.
*C12Q 1/6883* (2018.01)
*C12Q 1/6827* (2018.01)

(52) U.S. Cl.
CPC ......... *C12Q 1/6883* (2013.01); *C12Q 1/6827* (2013.01); *C12Q 2600/118* (2013.01)

(58) Field of Classification Search
None
See application file for complete search history.

(56) References Cited

U.S. PATENT DOCUMENTS

| 2010/0062947 | A1 | 3/2010 | De Laat | |
| 2010/0075861 | A1* | 3/2010 | De Laat | C12Q 1/6809 506/9 |

FOREIGN PATENT DOCUMENTS

| CN | 101238225 | 8/2008 |
| WO | 2016207653 | 12/2016 |
| WO | 2016207661 | 12/2016 |

OTHER PUBLICATIONS

Jakub et al (Melanoma Research. 2015. 25: 408-411).*
Crutchley et al (Biomarkers in Medicine. 2010. 4(4): 611-629).*
Klein (Acta Neuropathol Oct. 2016 132(4) pp. 503-514).*
Castillo (Scientific Reports 2017 7:17762 pp. 1-16).*
Announcement of Mar. 1, 2012 on the Oxford BioDynamics Website, "Parkinson's disease completed successfully".
Salter, et al., "Epigenetic signatures and early detection of neurodegenerative diseases", The Lancet Neurology Conference; Oct. 19-21, 2016; London, United Kingdom.
Hunter, et al., "Epigenetic footprints for neurodegenerative and autoimmune conditions: a comparative analysis", Oxford BioDynamics, published Oct. 21, 2016.
English translation of description and claims of CN101238225 (Univ Erasmus Medical CT [NL]).
Simonis, et al., "Nuclear organization of active and inactive chromatin domains uncovered by chromosome conformation capture-on-chip (4C)", Nature Genetics, Nature Publishing Group, NY, (Nov. 1, 2006), vol. 38, No. 11, pp. 1348-1354.
Carini, et al., "Epigenetic Chromosome Conformations Predict MTX Responsiveness in Early Rheumatoid Arthritis Patients", Annual Meeting of the American-College-of-Rheumatology (ACR) and Association-of-Rheumatology-Health, San Francisco, CA, 2015, Abstract No. 3256, (Sep. 29, 2015).
Kikuchi, et al., "Identification Of Chromosomal Regions Interacting With Susceptibility Loci For Alzheimer's Disease", Alzheimer's & Dementia: The Journal Of The Alzheimer's Association, (Jul. 24, 2016), vol. 12, No. 7, doi:10.1016/J.JALZ.2016.06.876, ISSN 1552-5260.
Crutchley, et al., "Chromatin Conformation Signatures: Ideal Human Disease Biomarkers?", Biomarkers in Medicine, (Aug. 1, 2010), vol. 4, No. 4, doi:10.2217/bmm.10.68, ISSN 1752-0363, pp. 611-629.
Sanchez-Mut, et al., "Epigenetic Alterations in Alzheimer's Disease", Frontiers in Behavioral Neuroscience, (Dec. 17, 2015), vol. 9.

* cited by examiner

*Primary Examiner* — Amanda Haney
(74) *Attorney, Agent, or Firm* — FisherBroyles, LLP; Victoria L. Boyd; Adelaide K. Leitzel

(57) ABSTRACT

The invention provides a method of determining the epigenetic chromosome interactions which are relevant to an epigenetic test for a neurodegenerative condition.

1 Claim, 3 Drawing Sheets

Specification includes a Sequence Listing.

A

B

A

B

Alzheimer's samples       Control samples

SEQUENCE LISTING

<160> NUMBER OF SEQ ID NOS: 126

<210> SEQ ID NO 1
<211> LENGTH: 60
<212> TYPE: DNA
<213> ORGANISM: Homo sapiens

<400> SEQUENCE: 1
ggcaggcaga ttacttgagg ttaggaattc gatgccgata gagtaaaaag cattctctgt    60

<210> SEQ ID NO 2
<211> LENGTH: 60
<212> TYPE: DNA
<213> ORGANISM: Homo sapiens

<400> SEQUENCE: 2
tttattaaaa atcactgaat tatatggttc gatgaaaaat attctttaga tctaagacct    60

<210> SEQ ID NO 3
<211> LENGTH: 60
<212> TYPE: DNA
<213> ORGANISM: Homo sapiens

```
<400> SEQUENCE: 3
aatgtaattg atctgggact ctgccacctc gaaaagagct gccctcccct ggctgctgtg    60

<210> SEQ ID NO 4
<211> LENGTH: 60
<212> TYPE: DNA
<213> ORGANISM: Homo sapiens

<400> SEQUENCE: 4
catacacaaa gcaatctgag atggattatc gaagtaaaaa ttttttacaga ttctctaagt   60

<210> SEQ ID NO 5
<211> LENGTH: 60
<212> TYPE: DNA
<213> ORGANISM: Homo sapiens

<400> SEQUENCE: 5
ggcagttgga tcatttgagt ccaagagttc gacactctca ttctgattct gtttgaaccc    60

<210> SEQ ID NO 6
<211> LENGTH: 60
<212> TYPE: DNA
<213> ORGANISM: Homo sapiens

<400> SEQUENCE: 6
agagggccca agtgtgactc tcaggttttc gactccctta gaaacatgca gttgttgttt    60

<210> SEQ ID NO 7
<211> LENGTH: 60
<212> TYPE: DNA
<213> ORGANISM: Homo sapiens

<400> SEQUENCE: 7
ttctagggtg ttacatttca aagaattttc gacttgaact tctgcctctc tatttgtatc    60

<210> SEQ ID NO 8
<211> LENGTH: 60
<212> TYPE: DNA
<213> ORGANISM: Homo sapiens

<400> SEQUENCE: 8
aagactgtct cccagatatc ttgctcattc gaagactgtc ttgctagaaa gaatattctt    60

<210> SEQ ID NO 9
<211> LENGTH: 60
<212> TYPE: DNA
<213> ORGANISM: Homo sapiens

<400> SEQUENCE: 9
tttattaaaa atcactgaat tatatggttc gattcacagt ctcttcattt gatcagaatc    60

<210> SEQ ID NO 10
<211> LENGTH: 60
<212> TYPE: DNA
<213> ORGANISM: Homo sapiens

<400> SEQUENCE: 10
agcagggtgt ggtgatgaag aggctgactc gataaacagc aaagttcctt tcccagccta    60

<210> SEQ ID NO 11
<211> LENGTH: 60
<212> TYPE: DNA
<213> ORGANISM: Homo sapiens
```

<400> SEQUENCE: 11
tttattaaaa atcactgaat tatatggttc gatttccagt acaactctat gaagaagtta        60

<210> SEQ ID NO 12
<211> LENGTH: 60
<212> TYPE: DNA
<213> ORGANISM: Homo sapiens

<400> SEQUENCE: 12
aaacagatgt gagatgatca gatttacatc gatagtatta tacgtggtca ttagcctcag        60

<210> SEQ ID NO 13
<211> LENGTH: 60
<212> TYPE: DNA
<213> ORGANISM: Homo sapiens

<400> SEQUENCE: 13 gctggggtc tcatcattct tccctcctc gactcttctc tgtcacccat tattcaatct          60

<210> SEQ ID NO 14
<211> LENGTH: 60
<212> TYPE: DNA
<213> ORGANISM: Homo sapiens

<400> SEQUENCE: 14
gaaaagaccc ttcaagcaga tggagagttc gagtcttcct agctctgtgt ccttgggcaa        60

<210> SEQ ID NO 15
<211> LENGTH: 60
<212> TYPE: DNA
<213> ORGANISM: Homo sapiens

<400> SEQUENCE: 15
ccataaaagg agggcaatgg aagaagagtc gactatttta tttttgtag agcgagatc         60

<210> SEQ ID NO 16
<211> LENGTH: 60
<212> TYPE: DNA
<213> ORGANISM: Homo sapiens

<400> SEQUENCE: 16
gaaaagaccc ttcaagcaga tggagagttc gattacctca aacaaagagg aatagcacta        60

<210> SEQ ID NO 17
<211> LENGTH: 60
<212> TYPE: DNA
<213> ORGANISM: Homo sapiens

<400> SEQUENCE: 17
atgacaagtg aatgaagctg aatatgtatc gacttctctc tgccacccc aactgtgagc        60

<210> SEQ ID NO 18
<211> LENGTH: 60
<212> TYPE: DNA
<213> ORGANISM: Homo sapiens

<400> SEQUENCE: 18
gtagtatgta gtggttacag catgatcttc gacttctctc tgccacccc aactgtgagc        60

<210> SEQ ID NO 19
<211> LENGTH: 60
<212> TYPE: DNA
<213> ORGANISM: Homo sapiens

<400> SEQUENCE: 19
ggcaggcaga ttacttgagg ttaggaattc gattctgact taagagacat aaacaaggaa    60

<210> SEQ ID NO 20
<211> LENGTH: 60
<212> TYPE: DNA
<213> ORGANISM: Homo sapiens

<400> SEQUENCE: 20
cctcatttac aaatgagaaa actaagagtc gaaagaaaat attcttcttt cctgaccatt    60

<210> SEQ ID NO 21
<211> LENGTH: 60
<212> TYPE: DNA
<213> ORGANISM: Homo sapiens

<400> SEQUENCE: 21
gtgtggccta atcaagaacc aatcagagtc gaactcatca tcctccctcc ccgccccacc    60

<210> SEQ ID NO 22
<211> LENGTH: 60
<212> TYPE: DNA
<213> ORGANISM: Homo sapiens

<400> SEQUENCE: 22
tgaatgagtc acttaatttg agtttgtatc gactcactgt actccagcct ggcaacagag    60

<210> SEQ ID NO 23
<211> LENGTH: 60
<212> TYPE: DNA
<213> ORGANISM: Homo sapiens

<400> SEQUENCE: 23
taccttcttt caatccggat attttcagtc gatgtaagag taacatatat tgttcaatat    60

<210> SEQ ID NO 24
<211> LENGTH: 60
<212> TYPE: DNA
<213> ORGANISM: Homo sapiens

<400> SEQUENCE: 24
gaaacaggtg ggtcatgagg tcaagagatc gatttattta ttttttcatt catcttcata    60

<210> SEQ ID NO 25
<211> LENGTH: 60
<212> TYPE: DNA
<213> ORGANISM: Homo sapiens

<400> SEQUENCE: 25
attattttcc ttctgcctta atcctctttc gacgctcctc ttcctgtatg catggtttct    60

<210> SEQ ID NO 26
<211> LENGTH: 60
<212> TYPE: DNA
<213> ORGANISM: Homo sapiens

<400> SEQUENCE: 26
ctgacaaacc acttagcttg tgtgatattc gactggctga caagtacccc cagaccagaa    60

<210> SEQ ID NO 27
<211> LENGTH: 60
<212> TYPE: DNA
<213> ORGANISM: Homo sapiens

<400> SEQUENCE: 27
acacgataaa agcttcaaag agaaaatgtc gatctggact ctgcctgccc ctacttcatc    60

<210> SEQ ID NO 28
<211> LENGTH: 60
<212> TYPE: DNA
<213> ORGANISM: Homo sapiens

<400> SEQUENCE: 28
gaagataaaa agctcaaaat gaatgaactc gatgcctgcc tcccacctttt ctgagttgag    60

<210> SEQ ID NO 29
<211> LENGTH: 60
<212> TYPE: DNA
<213> ORGANISM: Homo sapiens

<400> SEQUENCE: 29
gaaaagaccc ttcaagcaga tggagagttc gaaggaagca ttcagccatt attcactaag    60

<210> SEQ ID NO 30
<211> LENGTH: 60
<212> TYPE: DNA
<213> ORGANISM: Homo sapiens

<400> SEQUENCE: 30
taggtgggtg ggttacgagg ccagaagatc gatacaaact caaattaagt gactcattca    60

<210> SEQ ID NO 31
<211> LENGTH: 60
<212> TYPE: DNA
<213> ORGANISM: Homo sapiens

<400> SEQUENCE: 31
caagtgcatt cccatgtggg accttctttc gagcagggta gtgaatgttt ggggtagttt    60

<210> SEQ ID NO 32
<211> LENGTH: 60
<212> TYPE: DNA
<213> ORGANISM: Homo sapiens

<400> SEQUENCE: 32
cagggtgctg gaaaatgccc actttgcctc gagcttgcgt cactgcactc cagcctaggc    60

<210> SEQ ID NO 33
<211> LENGTH: 60
<212> TYPE: DNA
<213> ORGANISM: Homo sapiens

<400> SEQUENCE: 33
ttatactaca gggactcttt gatctgggtc gaaaaggtgc acaaatgaaa agggtaccgc    60

<210> SEQ ID NO 34
<211> LENGTH: 60
<212> TYPE: DNA
<213> ORGANISM: Homo sapiens

<400> SEQUENCE: 34
ctggcaagtc tcagctcttt gctagtcatc gactccttcc ctgtcctgct tccattgttt    60

<210> SEQ ID NO 35
<211> LENGTH: 60
<212> TYPE: DNA
<213> ORGANISM: Homo sapiens

<400> SEQUENCE: 35
gcctgcagga tccctgggca agcgtgcttc gaggcacccc atccccatcc ccactctgtc        60

<210> SEQ ID NO 36
<211> LENGTH: 60
<212> TYPE: DNA
<213> ORGANISM: Homo sapiens

<400> SEQUENCE: 36
ctgtcagtta cagaggaaga ctgctgtgtc gacctcctcc tcctgcctca gctcccaagc        60

<210> SEQ ID NO 37
<211> LENGTH: 60
<212> TYPE: DNA
<213> ORGANISM: Homo sapiens

<400> SEQUENCE: 37
taccttcttt caatccggat attttcagtc gatgtatatc cgtgaacttt ggggtaacat        60

<210> SEQ ID NO 38
<211> LENGTH: 60
<212> TYPE: DNA
<213> ORGANISM: Homo sapiens

<400> SEQUENCE: 38
agcaggcaga tcacttaagg acaagagttc gaaatcattt ctgatggaag gaaaggaaga        60

<210> SEQ ID NO 39
<211> LENGTH: 60
<212> TYPE: DNA
<213> ORGANISM: Homo sapiens

<400> SEQUENCE: 39
gagcagctgc ccagaatctg tcttgtcatc gaccctctgt gcctcagttt ccttatccag        60

<210> SEQ ID NO 40
<211> LENGTH: 60
<212> TYPE: DNA
<213> ORGANISM: Homo sapiens

<400> SEQUENCE: 40
gagtagtggt gtcttctcaa gaggaaaatc gattacatat taaggaattc tggaagatac        60

<210> SEQ ID NO 41
<211> LENGTH: 60
<212> TYPE: DNA
<213> ORGANISM: Homo sapiens

<400> SEQUENCE: 41
taactaagtg caaatgttct accagcattc gagaataaaa tgtcctttgt agcatgcttt        60

<210> SEQ ID NO 42
<211> LENGTH: 60
<212> TYPE: DNA
<213> ORGANISM: Homo sapiens

<400> SEQUENCE: 42
ccaaatccga acctcctctg tgaagcattc gagttgttgc caccccaccc tcctcaaacc        60

<210> SEQ ID NO 43
<211> LENGTH: 19
<212> TYPE: DNA
<213> ORGANISM: Homo sapiens

```
<400> SEQUENCE: 43
tcactctccc ttccctctg                                              19

<210> SEQ ID NO 44
<211> LENGTH: 19
<212> TYPE: DNA
<213> ORGANISM: Homo sapiens

<400> SEQUENCE: 44
aatgcagatt tgtgcttgc                                              19

<210> SEQ ID NO 45
<211> LENGTH: 20
<212> TYPE: DNA
<213> ORGANISM: Homo sapiens

<400> SEQUENCE: 45
gaaccaccat ttggtgaaag                                             20

<210> SEQ ID NO 46
<211> LENGTH: 18
<212> TYPE: DNA
<213> ORGANISM: Homo sapiens

<400> SEQUENCE: 46
ccacctcaca ccatacac                                               18

<210> SEQ ID NO 47
<211> LENGTH: 20
<212> TYPE: DNA
<213> ORGANISM: Homo sapiens

<400> SEQUENCE: 47
aaagatgagg ccgggtatgg                                             20

<210> SEQ ID NO 48
<211> LENGTH: 22
<212> TYPE: DNA
<213> ORGANISM: Homo sapiens

<400> SEQUENCE: 48
gtaagagtga tgatgcttgg ac                                          22

<210> SEQ ID NO 49
<211> LENGTH: 21
<212> TYPE: DNA
<213> ORGANISM: Homo sapiens

<400> SEQUENCE: 49
tgattacaca caacactgac g                                           21

<210> SEQ ID NO 50
<211> LENGTH: 20
<212> TYPE: DNA
<213> ORGANISM: Homo sapiens

<400> SEQUENCE: 50
gcagagaatg gagccaaatg                                             20

<210> SEQ ID NO 51
<211> LENGTH: 21
<212> TYPE: DNA
<213> ORGANISM: Homo sapiens
```

```
<400> SEQUENCE: 51
gtagatagtg gtggtgattg c                                          21

<210> SEQ ID NO 52
<211> LENGTH: 21
<212> TYPE: DNA
<213> ORGANISM: Homo sapiens

<400> SEQUENCE: 52
cggaaaccca agagtgttta g                                          21

<210> SEQ ID NO 53
<211> LENGTH: 21
<212> TYPE: DNA
<213> ORGANISM: Homo sapiens

<400> SEQUENCE: 53
gaataactgc tggtgggtat g                                          21

<210> SEQ ID NO 54
<211> LENGTH: 19
<212> TYPE: DNA
<213> ORGANISM: Homo sapiens

<400> SEQUENCE: 54
agatgagacc agagggaag                                             19

<210> SEQ ID NO 55
<211> LENGTH: 19
<212> TYPE: DNA
<213> ORGANISM: Homo sapiens

<400> SEQUENCE: 55
actgagcgaa acagaaagg                                             19

<210> SEQ ID NO 56
<211> LENGTH: 20
<212> TYPE: DNA
<213> ORGANISM: Homo sapiens

<400> SEQUENCE: 56
atgacccatt tgcagcgtga                                            20

<210> SEQ ID NO 57
<211> LENGTH: 24
<212> TYPE: DNA
<213> ORGANISM: Homo sapiens

<400> SEQUENCE: 57
gctcacatca aatctcaaag ggca                                       24

<210> SEQ ID NO 58
<211> LENGTH: 20
<212> TYPE: DNA
<213> ORGANISM: Homo sapiens

<400> SEQUENCE: 58
agcgtgacag agcccagttc                                            20

<210> SEQ ID NO 59
<211> LENGTH: 22
<212> TYPE: DNA
<213> ORGANISM: Homo sapiens
```

```
<400> SEQUENCE: 59
tcagcagtta cctcagagtc ct                                           22

<210> SEQ ID NO 60
<211> LENGTH: 20
<212> TYPE: DNA
<213> ORGANISM: Homo sapiens

<400> SEQUENCE: 60
ttgagaggcc cgtcatctgt                                              20

<210> SEQ ID NO 61
<211> LENGTH: 22
<212> TYPE: DNA
<213> ORGANISM: Homo sapiens

<400> SEQUENCE: 61
ggtggctcat accatagcac ca                                           22

<210> SEQ ID NO 62
<211> LENGTH: 20
<212> TYPE: DNA
<213> ORGANISM: Homo sapiens

<400> SEQUENCE: 62
gctcactgcc atcctgcaac                                              20

<210> SEQ ID NO 63
<211> LENGTH: 20
<212> TYPE: DNA
<213> ORGANISM: Homo sapiens

<400> SEQUENCE: 63
attcgctcgc cacatctcct                                              20

<210> SEQ ID NO 64
<211> LENGTH: 21
<212> TYPE: DNA
<213> ORGANISM: Homo sapiens

<400> SEQUENCE: 64
gccatgcagt gtctgatagg t                                            21

<210> SEQ ID NO 65
<211> LENGTH: 24
<212> TYPE: DNA
<213> ORGANISM: Homo sapiens

<400> SEQUENCE: 65
attccattgt gtccctctgt tcct                                         24

<210> SEQ ID NO 66
<211> LENGTH: 25
<212> TYPE: DNA
<213> ORGANISM: Homo sapiens

<400> SEQUENCE: 66
ttgaattcct gggtgtgagt tttgc                                        25

<210> SEQ ID NO 67
<211> LENGTH: 22
<212> TYPE: DNA
<213> ORGANISM: Homo sapiens
```

-continued

<400> SEQUENCE: 67
ccaggcactt tctctcggtt tt                                      22

<210> SEQ ID NO 68
<211> LENGTH: 20
<212> TYPE: DNA
<213> ORGANISM: Homo sapiens

<400> SEQUENCE: 68
ccggattgtc cagcgtcact                                         20

<210> SEQ ID NO 69
<211> LENGTH: 22
<212> TYPE: DNA
<213> ORGANISM: Homo sapiens

<400> SEQUENCE: 69
ccgcaacagg acaattgcat ca                                      22

<210> SEQ ID NO 70
<211> LENGTH: 21
<212> TYPE: DNA
<213> ORGANISM: Homo sapiens

<400> SEQUENCE: 70
cagagaggct gtccctagca c                                       21

<210> SEQ ID NO 71
<211> LENGTH: 19
<212> TYPE: DNA
<213> ORGANISM: Homo sapiens

<400> SEQUENCE: 71
gactctggac agccggacc                                          19

<210> SEQ ID NO 72
<211> LENGTH: 22
<212> TYPE: DNA
<213> ORGANISM: Homo sapiens

<400> SEQUENCE: 72
catcaaataa accagcagac ag                                      22

<210> SEQ ID NO 73
<211> LENGTH: 20
<212> TYPE: DNA
<213> ORGANISM: Homo sapiens

<400> SEQUENCE: 73
gttattgtcg ctgctgtttg                                         20

<210> SEQ ID NO 74
<211> LENGTH: 21
<212> TYPE: DNA
<213> ORGANISM: Homo sapiens

<400> SEQUENCE: 74
cagttcacaa tggaggagaa g                                       21

<210> SEQ ID NO 75
<211> LENGTH: 19
<212> TYPE: DNA
<213> ORGANISM: Homo sapiens

```
<400> SEQUENCE: 75
gtctcatttc caccacctc                                                19

<210> SEQ ID NO 76
<211> LENGTH: 20
<212> TYPE: DNA
<213> ORGANISM: Homo sapiens

<400> SEQUENCE: 76
gtctctcaca gtcaagatgc                                               20

<210> SEQ ID NO 77
<211> LENGTH: 19
<212> TYPE: DNA
<213> ORGANISM: Homo sapiens

<400> SEQUENCE: 77
agagagaagg ctggacttg                                                19

<210> SEQ ID NO 78
<211> LENGTH: 20
<212> TYPE: DNA
<213> ORGANISM: Homo sapiens

<400> SEQUENCE: 78
gagacactca ggcttctttc                                               20

<210> SEQ ID NO 79
<211> LENGTH: 19
<212> TYPE: DNA
<213> ORGANISM: Homo sapiens

<400> SEQUENCE: 79
cggtggatca ttccattgt                                                19

<210> SEQ ID NO 80
<211> LENGTH: 23
<212> TYPE: DNA
<213> ORGANISM: Homo sapiens

<400> SEQUENCE: 80
acagggatgg atatttggtg gag                                           23

<210> SEQ ID NO 81
<211> LENGTH: 20
<212> TYPE: DNA
<213> ORGANISM: Homo sapiens

<400> SEQUENCE: 81
caggacttga gcttggaggg                                               20

<210> SEQ ID NO 82
<211> LENGTH: 20
<212> TYPE: DNA
<213> ORGANISM: Homo sapiens

<400> SEQUENCE: 82
gcagccacag aaatgagtag                                               20

<210> SEQ ID NO 83
<211> LENGTH: 18
<212> TYPE: DNA
<213> ORGANISM: Homo sapiens
```

-continued

```
<400> SEQUENCE: 83
acgtgctgcc caattaac                                              18

<210> SEQ ID NO 84
<211> LENGTH: 20
<212> TYPE: DNA
<213> ORGANISM: Homo sapiens

<400> SEQUENCE: 84
tagctttcaa ttccgtagcc                                            20

<210> SEQ ID NO 85
<211> LENGTH: 25
<212> TYPE: DNA
<213> ORGANISM: Homo sapiens

<400> SEQUENCE: 85
ggtctgatta tactgatttg gatgc                                      25

<210> SEQ ID NO 86
<211> LENGTH: 21
<212> TYPE: DNA
<213> ORGANISM: Homo sapiens

<400> SEQUENCE: 86
cagctagtgt tgaggtctta g                                          21

<210> SEQ ID NO 87
<211> LENGTH: 20
<212> TYPE: DNA
<213> ORGANISM: Homo sapiens

<400> SEQUENCE: 87
agaaagaaca gtgtctgtgg                                            20

<210> SEQ ID NO 88
<211> LENGTH: 18
<212> TYPE: DNA
<213> ORGANISM: Homo sapiens

<400> SEQUENCE: 88
gcctgcaaag cctaaatg                                              18

<210> SEQ ID NO 89
<211> LENGTH: 20
<212> TYPE: DNA
<213> ORGANISM: Homo sapiens

<400> SEQUENCE: 89
cccaacagag tacaggcacc                                            20

<210> SEQ ID NO 90
<211> LENGTH: 24
<212> TYPE: DNA
<213> ORGANISM: Homo sapiens

<400> SEQUENCE: 90
caggagatag aaatctggga attg                                       24

<210> SEQ ID NO 91
<211> LENGTH: 22
<212> TYPE: DNA
<213> ORGANISM: Homo sapiens
```

<400> SEQUENCE: 91
gaaatgaact gaagcatgat gg						22

<210> SEQ ID NO 92
<211> LENGTH: 22
<212> TYPE: DNA
<213> ORGANISM: Homo sapiens

<400> SEQUENCE: 92
ggccataaac tcaaacctag tg						22

<210> SEQ ID NO 93
<211> LENGTH: 19
<212> TYPE: DNA
<213> ORGANISM: Homo sapiens

<400> SEQUENCE: 93
ccactcaaac gctcatctc						19

<210> SEQ ID NO 94
<211> LENGTH: 22
<212> TYPE: DNA
<213> ORGANISM: Homo sapiens

<400> SEQUENCE: 94
acactgtaga ggagtggtta tc						22

<210> SEQ ID NO 95
<211> LENGTH: 23
<212> TYPE: DNA
<213> ORGANISM: Homo sapiens

<400> SEQUENCE: 95
gtatcttgtt cctcccactt tac						23

<210> SEQ ID NO 96
<211> LENGTH: 20
<212> TYPE: DNA
<213> ORGANISM: Homo sapiens

<400> SEQUENCE: 96
cactggccct aggatttaag						20

<210> SEQ ID NO 97
<211> LENGTH: 20
<212> TYPE: DNA
<213> ORGANISM: Homo sapiens

<400> SEQUENCE: 97
aggagagagt gtagtcaagg						20

<210> SEQ ID NO 98
<211> LENGTH: 23
<212> TYPE: DNA
<213> ORGANISM: Homo sapiens

<400> SEQUENCE: 98
ggtagactag gcactgcttc agg						23

<210> SEQ ID NO 99
<211> LENGTH: 24
<212> TYPE: DNA
<213> ORGANISM: Homo sapiens

```
<400> SEQUENCE: 99
gtggctgtaa ggacatgggt agaa                                          24

<210> SEQ ID NO 100
<211> LENGTH: 21
<212> TYPE: DNA
<213> ORGANISM: Homo sapiens

<400> SEQUENCE: 100
ttgaggccca gagcaacttc t                                             21

<210> SEQ ID NO 101
<211> LENGTH: 21
<212> TYPE: DNA
<213> ORGANISM: Homo sapiens

<400> SEQUENCE: 101
tgcttggagg cagatacccT c                                             21

<210> SEQ ID NO 102
<211> LENGTH: 21
<212> TYPE: DNA
<213> ORGANISM: Homo sapiens

<400> SEQUENCE: 102
gtgcttggag gcagataccc t                                             21

<210> SEQ ID NO 103
<211> LENGTH: 21
<212> TYPE: DNA
<213> ORGANISM: Homo sapiens

<400> SEQUENCE: 103
ccaacagagt acaggcaccc a                                             21

<210> SEQ ID NO 104
<211> LENGTH: 20
<212> TYPE: DNA
<213> ORGANISM: Homo sapiens

<400> SEQUENCE: 104
cagaccccct tggggaacat                                               20

<210> SEQ ID NO 105
<211> LENGTH: 20
<212> TYPE: DNA
<213> ORGANISM: Homo sapiens

<400> SEQUENCE: 105
gcacctgggg gagtagaagg                                               20

<210> SEQ ID NO 106
<211> LENGTH: 23
<212> TYPE: DNA
<213> ORGANISM: Homo sapiens

<400> SEQUENCE: 106
gagtgttaaa caattgaggg gga                                           23

<210> SEQ ID NO 107
<211> LENGTH: 21
<212> TYPE: DNA
<213> ORGANISM: Homo sapiens
```

```
<400> SEQUENCE: 107
tttggggtcc cactttgagg g                                              21

<210> SEQ ID NO 108
<211> LENGTH: 21
<212> TYPE: DNA
<213> ORGANISM: Homo sapiens

<400> SEQUENCE: 108
agtccttggc aggtaggtag c                                              21

<210> SEQ ID NO 109
<211> LENGTH: 24
<212> TYPE: DNA
<213> ORGANISM: Homo sapiens

<400> SEQUENCE: 109
ggggaagagg gcttaccaat agag                                           24

<210> SEQ ID NO 110
<211> LENGTH: 20
<212> TYPE: DNA
<213> ORGANISM: Homo sapiens

<400> SEQUENCE: 110
agaacaccgc accgtctgtt                                                20

<210> SEQ ID NO 111
<211> LENGTH: 20
<212> TYPE: DNA
<213> ORGANISM: Homo sapiens

<400> SEQUENCE: 111
cgtgctgggt ggtgagtaac                                                20

<210> SEQ ID NO 112
<211> LENGTH: 22
<212> TYPE: DNA
<213> ORGANISM: Homo sapiens

<400> SEQUENCE: 112
ggccaacatg cccacattct ac                                             22

<210> SEQ ID NO 113
<211> LENGTH: 24
<212> TYPE: DNA
<213> ORGANISM: Homo sapiens

<400> SEQUENCE: 113
gatctagcaa atggccaagg ctta                                           24

<210> SEQ ID NO 114
<211> LENGTH: 22
<212> TYPE: DNA
<213> ORGANISM: Homo sapiens

<400> SEQUENCE: 114
ctgatgaagg agatgcatag ag                                             22

<210> SEQ ID NO 115
<211> LENGTH: 21
<212> TYPE: DNA
<213> ORGANISM: Homo sapiens
```

<400> SEQUENCE: 115
tccatctgtg tttctcaagt c                21

<210> SEQ ID NO 116
<211> LENGTH: 21
<212> TYPE: DNA
<213> ORGANISM: Homo sapiens

<400> SEQUENCE: 116
gagatggaaa gggaaggaaa g                21

<210> SEQ ID NO 117
<211> LENGTH: 23
<212> TYPE: DNA
<213> ORGANISM: Homo sapiens

<400> SEQUENCE: 117
catctactgg gatagaagtc aag              23

<210> SEQ ID NO 118
<211> LENGTH: 22
<212> TYPE: DNA
<213> ORGANISM: Homo sapiens

<400> SEQUENCE: 118
gtgcaaggaa tttatgaaag gg               22

<210> SEQ ID NO 119
<211> LENGTH: 18
<212> TYPE: DNA
<213> ORGANISM: Homo sapiens

<400> SEQUENCE: 119
aagaaagcca gggaggag                    18

<210> SEQ ID NO 120
<211> LENGTH: 20
<212> TYPE: DNA
<213> ORGANISM: Homo sapiens

<400> SEQUENCE: 120
tctgtctgct tcagctttac                  20

<210> SEQ ID NO 121
<211> LENGTH: 20
<212> TYPE: DNA
<213> ORGANISM: Homo sapiens

<400> SEQUENCE: 121
gggctctgaa ctgaatgtag                  20

<210> SEQ ID NO 122
<211> LENGTH: 20
<212> TYPE: DNA
<213> ORGANISM: Homo sapiens

<400> SEQUENCE: 122
gcccactgac acaaagactc                  20

<210> SEQ ID NO 123
<211> LENGTH: 22
<212> TYPE: DNA
<213> ORGANISM: Homo sapiens

```
<400> SEQUENCE: 123
ctgtgccaat aactctcagt gc                                              22

<210> SEQ ID NO 124
<211> LENGTH: 21
<212> TYPE: DNA
<213> ORGANISM: Homo sapiens

<400> SEQUENCE: 124
tcgcatgtag atccaacaaa g                                               21

<210> SEQ ID NO 125
<211> LENGTH: 20
<212> TYPE: DNA
<213> ORGANISM: Homo sapiens

<400> SEQUENCE: 125
tcaagtgtga catgctgaag                                                 20

<210> SEQ ID NO 126
<211> LENGTH: 19
<212> TYPE: DNA
<213> ORGANISM: Homo sapiens

<400> SEQUENCE: 126
cactggtggt cccatttac                                                  19
```

TYPING METHOD

CROSS-REFERENCE TO RELATED APPLICATIONS

The present invention is a continuation application of International Patent Application No. PCT/GB2016/054076, filed Dec. 23, 2016, which is incorporated herein in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Jun. 18, 2019, is named 12440-002US1_SeqListing and is 18.4 kilobytes in size.

FIELD OF THE INVENTION

The invention relates to detecting chromosome interactions.

BACKGROUND OF THE INVENTION

Present diagnosis of neurodegenerative disease is often difficult, particularly at the early stages. Usually diagnosis happens when symptoms, such as a deterioration in mental abilities, have started to manifest.

SUMMARY OF THE INVENTION

The inventors have identified regions of the genome where chromosomal interactions are relevant to neurodegenerative conditions. The inventors work allows typing of individuals into subgroups with different neurodegenerative characteristics based on chromosome interactions.

Accordingly the method provides a method of determining the epigenetic chromosome interactions which are relevant to an epigenetic test for a neurodegenerative condition, wherein the test distinguishes between subgroups, comprising contacting a first set of nucleic acids from the subgroups with a second set of nucleic acids representing an index population of chromosome interactions, and allowing complementary sequences to hybridise, wherein the nucleic acids in the first and second sets of nucleic acids represent a ligated product comprising sequences from both of the chromosome regions that have come together in the epigenetic chromosome interaction, and wherein the pattern of hybridisation between the first and second set of nucleic acids allows a determination of which epigenetic chromosome interactions are specific to subgroups in the population, wherein the subgroups differ in at least one characteristic relevant to the condition, optionally selected from diagnosis, prognosis, likelihood of developing and/or predisposition to the condition.

The invention also provides methods of determining a characteristic of a neurodegenerative condition in an individual comprising: (a) typing at least one chromosome interaction which has been identified by the above method, and/or (b) typing at least one chromosome interaction which is associated with a characteristic of a neurodegenerative condition, wherein said characteristic is optionally selected from diagnosis, prognosis, likelihood of developing, predisposition to and/or early pre-symptomatic detection of the condition, and wherein said association may be presence or absence of the chromosome interaction. The condition is preferably a dementia or cognitive impairment, preferably Alzheimer's disease.

DETAILED DESCRIPTION OF THE INVENTION

Figure 1:
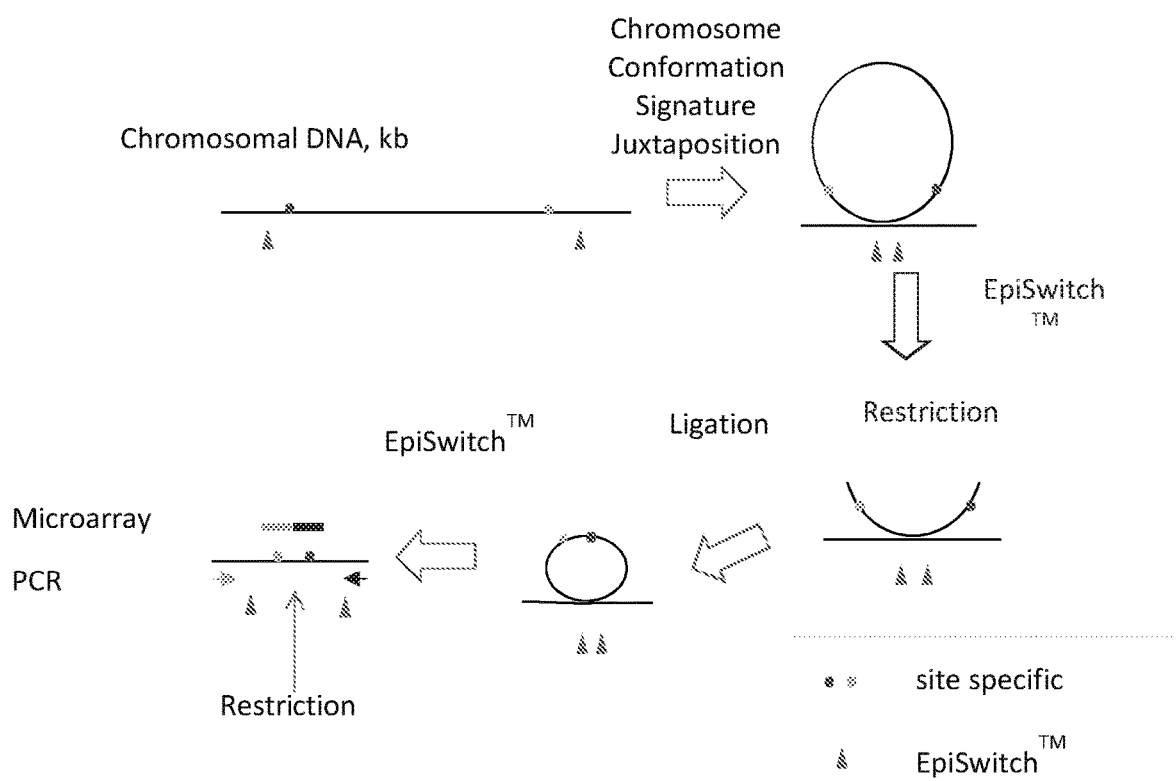
FIG. 1 is a Schematic diagram of the 3C extraction method. 3C means chromatin conformation capture, or chromosome conformation capture.

The invention has several different aspects, including inter alia:
- a method for identifying epigenetic chromosome interactions relevant to different subgroups;
- a method which selects a subgroup with particular characteristics, and/or a method of identifying the subgroup of an individual;
- a method of identifying a drug that can be used to treat or prevent a neurodegenerative condition.

Regions Relevant to Neurodegenerative Disease

The invention concerns typing of chromosome interactions at disease-associated or epigenetically active regions relevant to a neurodegenerative condition. In such regions chromosome interactions will occur which affect an aspect of the condition. The chromosome interactions may affect or be associated with having or being susceptible to the condition or prognosis (relating to outcome). Therefore the chromosome interactions may relevant to diagnosis or likelihood of developing the diseases. Specific chromosome interactions, genes and regions relevant to neurodegenerative conditions are disclosed in the tables herein.

The chromosome interaction which is typed may or may not be one which occurs between a gene (including coding sequence) and its regulatory region, such as a promoter. The chromosome interaction which is typed may or may not be one which is inherited, for example an inherited imprinted characteristic of a gene region. The chromosome interaction may or may not be one which occurs between two regulatory regions, for example such as an interaction between an enhancer and a promoter or an interaction between a promoter and another promoter. The chromosome interaction may be associated with deregulation of a gene, for example a change in the activity (such as an increase or decrease) in an enhancer.

Prognosis

Prognostic as used herein relates to predicting the likely course of a medical condition, such as one or more outcomes. A prognostic factor is typically a clinical or biologic characteristic that is objectively measurable and that provides information on the likely outcome of the neurodegenerative condition.

Epigenetic Interactions

As used herein, the term 'epigenetic' interactions typically refers to interactions between distal regions of a locus on a chromosome, said interactions being dynamic and altering, forming or breaking depending upon the status of the region of the chromosome.

In particular methods of the invention chromosome interactions are detected by first generating a ligated nucleic acid that comprises sequence from both regions of the chromosomes that are part of the interactions. In such methods the regions can be cross-linked by any suitable means. In a preferred embodiment, the interactions are cross-linked using formaldehyde, but may also be cross-linked by any aldehyde, or D-Biotinoyl-e-aminocaproic acid-N-hydroxysuccinimide ester or Digoxigenin-3-O-methylcarbonyl-e-aminocaproic acid-N-hydroxysuccinimide ester. Paraformaldehyde is preferred and can crosslink DNA chains which are 4 Angstroms apart.

The chromosome interaction may reflect the status of the region of the chromosome, for example, if it is being transcribed or repressed. Chromosome interactions which are specific to subgroups as defined herein have been found to be stable, thus providing a reliable means of measuring the differences between the two subgroups.

In addition, chromosome interactions specific to a characteristic will normally occur early in a biological process, for example compared to other epigenetic markers such as methylation or changes to binding of histone proteins. Thus the method of the invention is able to detect early stages of a biological process. This allows early intervention (for example treatment) which may as a consequence be more effective. Furthermore there is little variation in the relevant chromosome interactions between individuals within the same subgroup. In the present invention typing of chromosome interactions allows early and/or presymptomatic diagnosis. In certain embodiments it allows detection of characteristics of the condition at least 1, 5, 10, 20 or 40 years before symptoms develop (where a year is defined as 365 days). Early or presymptomatic detection is particularly preferred for embodiments relating to Alzheimer's disease.

Location and Causes of Epigenetic Interactions

Epigenetic chromosomal interactions may overlap and include the regions of chromosomes shown to encode relevant or undescribed genes, but equally may be in intergenic regions. It should further be noted that the inventors have discovered that epigenetic interactions in all regions are equally important in determining the status of the chromosomal locus. These interactions are not necessarily in the coding region of a particular gene located at the locus and may be in intergenic regions. These interactions may or may not be long range interactions between genes and their regulatory elements. These interactions may or may not include promoter-promoter interactions and/or promoter-enhancer interactions. The chromosome interactions which are detected in the invention could be caused by changes to the underlying DNA sequence, by environmental factors, DNA methylation, non-coding antisense RNA transcripts, non-mutagenic carcinogens, histone modifications, chromatin remodelling and specific local DNA interactions. The changes which lead to the chromosome interactions may be caused by changes to the underlying nucleic acid sequence, which themselves do not directly affect a gene product or the mode of gene expression. Such changes may be for example, SNP's within and/or outside of the genes, gene fusions and/or deletions of intergenic DNA, microRNA, and non-coding RNA. For example, it is known that roughly 20% of SNPs are in non-coding regions, and therefore the method as described is also informative in non-coding situation. In one embodiment the regions of the chromosome which come together to form the interaction are less than 5 kb, 3 kb, 1 kb, 500 base pairs or 200 base pairs apart on the same chromosome. The regions of the chromosome which come together to form the interaction can be more than 5 kb, 10 kb, 50 kb, 100 kb, 200 kb, 500 kb, or more than 800 kb apart on the same chromosome, and can for example be 800 kb to 1,500 kb apart.

The chromosome interaction which is detected is preferably within any of the genes mentioned in the Tables herein. However it may also be upstream or downstream of the genes, for example up to 50,000, up to 30,000, up to 20,000, up to 10,000 or up to 5000 bases upstream or downstream from the gene or from the coding sequence.

Types of Clinical Situation

The aim of the present invention is to permit detection of chromosome interactions relevant to a characteristic that defines subgroups in the population. For example, this technology allows stratification based on biomarkers for specific phenotypes (e.g. relating to a neurodegenerative condition), i.e. by recognising a particular chromosome confirmation signature and/or a change in that particular signature.

The methods of the invention may be used in the context of specific characteristics relating to disease, such as diagnosis, prognosis, monitoring the course of disease, and/or identifying predisposition to disease. Therefore the methods may or may not be used for diagnosis of the presence of a specific condition. The methods of the invention can be used to type loci where the mechanisms of disease are unknown, unclear or complex. Detection of chromosome interactions provides an efficient way of following changes at the different levels of regulation, some of which are complex. For example in some cases around 37,000 non-coding RNAs can be activated by a single impulse.

Subgroups and Personalised Treatment

As used herein, a "subgroup" preferably refers to a population subgroup (a subgroup in a population), more preferably a subgroup in the population of a particular animal such as a particular eukaryote, or mammal (e.g. human, non-human, non-human primate, or rodent e.g. mouse or rat). Most preferably, a "subgroup" refers to a subgroup in the human population.

The invention includes detecting and treating particular subgroups in a population. Within such subgroups the characteristics discussed herein (such as cognitive deficit, or a diagnosis of a neurodegenerative condition) will be present or absent. Epigenetic interaction differences on a chromosome are, generally speaking, structural differences which exist at a genomic level. The inventors have discovered that these differ between subsets (for example two or at least two subsets) in a given population. Identifying these differences will allow physicians to categorize their patients as a part of one subset of the population as described in the method. The invention therefore provides physicians with a method of personalizing medicine for the patient based on their epigenetic chromosome interactions, and provide an alternative more effective treatment regime.

In another embodiment, threshold levels for determining to what extent a subject is defined as one subgroup and not the other of the population are applied. Typically a subgroup will be at least 1%, 5%, 10%, 30%, 50% or 80% of the general population.

Generating Ligated Nucleic Acids

Certain embodiments of the invention utilise ligated nucleic acids, in particular ligated DNA. These comprise sequences from both of the regions that come together in a chromosome interaction and therefore provide information about the interaction. The EpiSwitch™ method described herein uses generation of such ligated nucleic acids to detect chromosome interactions.

Thus a method of the invention may comprise a step of generating ligated nucleic acids (e.g. DNA) by:

(i) in vitro crosslinking of epigenetic chromosomal interactions present at the chromosomal locus;

(ii) optionally isolating the cross-linked DNA from said chromosomal locus;

(iii) subjecting said cross-linked DNA to cutting, for example by restriction digestion with an enzyme that cuts it at least once (in particular an enzyme that cuts at least once within said chromosomal locus);

(iv) ligating said cross-linked cleaved DNA ends (in particular to form DNA loops); and (v) identifying the presence of said ligated DNA and/or said DNA loops, in particular using techniques such as PCR, to identify the presence of a specific chromosomal interaction.

Any suitable technique may be used to detect the ligated nucleic acid, for example PCR (polymerase chain reaction) may be used to detect or identify the ligated nucleic acid. In this case the size of the PCR product produced may be indicative of the specific chromosome interaction which is present, and may therefore be used to identify the status of the locus. PCR may be used to detect and select biomarkers specific for particular phenotype subgroups versus controls. Any of the PCR primers or primer pairs disclosed herein may be used or variants of these such as homologues and/or fragments capable of amplifying the same ligated nucleic acid. Similarly any probe disclosed herein may be used, or a homologue and/or fragment of the probe capable of specifically binding the same ligated nucleic acid.

The skilled person will be aware of numerous restriction enzymes which can be used to cut the DNA within the chromosomal locus of interest. It will be apparent that the particular enzyme used will depend upon the locus studied and the sequence of the DNA located therein. A non-limiting example of a restriction enzyme which can be used to cut the DNA as described in the present invention is TaqI.

Embodiments such as EpiSwitch™ Technology

A part of the EpiSwitch™ Technology relates to the use of microarray EpiSwitch™ marker data in the detection of epigenetic chromosome conformation signatures. In one embodiment the EpiSwitch™ Array Platform can be used, however the invention is not restricted to this Array Platform. In one embodiment the invention is carried out using only a PCR-based technology.

Embodiments such as EpiSwitch™ which utilise ligated nucleic acids in the manner described herein have several advantages. They have a low level of stochastic noise, for example because the nucleic acid sequences from the first set of nucleic acids of the present invention either hybridise or fail to hybridise with the second set of nucleic acids. This provides a binary result permitting a relatively simple way to measure a complex mechanism at the epigenetic level. EpiSwitch™ technology also has fast processing time and low cost. In one embodiment the processing time is 3 to 6 hours.

Samples and Sample Treatment

The sample will contain DNA from the individual. It will normally contain cells. In one embodiment a sample is obtained by minimally invasive means, and may for example be blood. DNA may be extracted and cut up with a standard restriction enzyme. This can pre-determine which chromosome conformations are retained and will be detected with the EpiSwitch™ platforms. In one embodiment wherein the sample is a blood sample previously obtained from the patient, the described method is advantageous because the procedure is minimally invasive. Due to the synchronisation of chromosome interactions between tissues and blood, including horizontal transfer, a blood sample can be used to detect the chromosome interactions in tissues, such as tissues relevant to disease.

Properties of Nucleic Acids used in the Invention

The invention concerns nucleic acids. These may be the same as, or have any of the properties of, the first and second nucleic acids mentioned herein. The nucleic acids of the invention typically comprise two portions each comprising sequence from one of the two regions of the chromosome which come together in the chromosome interaction. Typically each portion is at least 8, 10, 15, 20, 30 or 40 nucleotides in length, for example 10 to 40 nucleotides in length. Preferred nucleic acids (including the first and/or second set of nucleic acids) comprise sequence from any of the genes mentioned in any of the tables. Preferred nucleic acids comprise any of the specific probe sequences and/or any of the primer sequences mentioned in any of the tables; or fragments and/or homologues of such sequences. Preferred ligated nucleic acids (including of the first or second set of nucleic acids) can be detected (for example specifically bind) by any of the probes, primers or primer pairs mentioned herein. Preferably the nucleic acids are DNA. It is understood that where a specific sequence is mentioned the invention may use the complementary sequence as required in the particular embodiment.

The Second Set of Nucleic Acids—the 'Index' Sequences

The second set of nucleic acid sequences has the function of being a set of index sequences, and is essentially a set of nucleic acid sequences which are suitable for identifying subgroup specific sequence. They can represents the 'background' chromosomal interactions and might be selected in some way or be unselected. They are in general a subset of all possible chromosomal interactions.

The second set of nucleic acids may be derived by any suitable method. They can be derived computationally or they may be based on chromosome interaction in individuals. They typically represent a larger population group than the first set of nucleic acids. In one particular embodiment, the second set of nucleic acids represents all possible epigenetic chromosomal interactions in a specific set of genes. In another particular embodiment, the second set of nucleic acids represents a large proportion of all possible epigenetic chromosomal interactions present in a population described herein. In one particular embodiment, the second set of nucleic acids represents at least 50% or at least 80% of epigenetic chromosomal interactions in at least 20, 50, 100 or 500 genes, for example in 20 to 100 or 50 to 500 genes.

The second set of nucleic acids typically represents at least 100 possible epigenetic chromosome interactions which modify, regulate or in any way mediate a disease state/phenotype in population. The second set of nucleic acids may represent chromosome interactions that affect a disease state in a species, for example comprising nucleic acids sequences which encode cytokines, kinases, or regulators associated with any disease state, predisposition to a disease or a disease phenotype. The second set of nucleic acids typically comprises sequences representing epigenetic interactions relevant and not relevant to the characteristic that defines the subgroup.

In one particular embodiment the second set of nucleic acids derive at least partially from naturally occurring sequences in a population, and are typically obtained by in silico methods. Said nucleic acids may further comprise single or multiple mutations in comparison to a corresponding portion of nucleic acids present in the naturally occurring nucleic acids. Mutations include deletions, substitutions and/or additions of one or more nucleotide base pairs. In one particular embodiment, the second set of nucleic acids may comprise sequence representing a homologue and/or orthologue with at least 70% sequence identity to the corresponding portion of nucleic acids present in the naturally occurring species. In another particular embodiment, at least 80% sequence identity or at least 90% sequence identity to the corresponding portion of nucleic acids present in the naturally occurring species is provided.

Properties of the Second Set of Nucleic Acids

In one particular embodiment, there are at least 100 different nucleic acid sequences in the second set of nucleic acids, preferably at least 1000, 2000 or 5000 different nucleic acids sequences, with up to 100,000, 1,000,000 or 10,000,000 different nucleic acid sequences. A typical number would be 100 to 1,000,000, such as 1,000 to 100,000 different nucleic acids sequences. All, or at least 90% or at least 50%, of these would correspond to different chromosomal interactions.

In one particular embodiment, the second set of nucleic acids represent chromosome interactions in at least 20 different loci or genes, preferably at least 40 different loci or genes, and more preferably at least 100, at least 500, at least 1000 or at least 5000 different loci or genes, such as 100 to 10,000 different loci or genes. The lengths of the second set of nucleic acids are suitable for them to specifically hybridise according to Watson Crick base pairing to the first set of nucleic acids to allow identification of chromosome interactions specific to subgroups. Typically the second set of nucleic acids will comprise two portions corresponding in sequence to the two chromosome regions which come together in the chromosome interaction. The second set of nucleic acids typically comprise nucleic acid sequences which are at least 10, preferably 20, and preferably still 30 bases (nucleotides) in length. In another embodiment, the nucleic acid sequences may be at the most 500, preferably at most 100, and preferably still at most 50 base pairs in length. In a preferred embodiment, the second set of nucleic acids comprises nucleic acid sequences of between 17 and 25 base pairs. In one embodiment at least 100, 80% or 50% of the second set of nucleic acid sequences have lengths as described above. Preferably the different nucleic acids do not have any overlapping sequences, for example at least 100%, 90%, 80% or 50% of the nucleic acids do not have the same sequence over at least 5 contiguous nucleotides.

Given that the second set of nucleic acids acts as an 'index' then the same set of second nucleic acids may be used with different sets of first nucleic acids which represent subgroups for different characteristics, i.e. the second set of nucleic acids may represent a 'universal' collection of nucleic acids which can be used to identify chromosome interactions relevant to different characteristics.

The First Set of Nucleic Acids

The first set of nucleic acids are normally from individuals known to be in two or more distinct subgroups defined by presence or absence of a characteristic relevant to a companion diagnostic, such as any such characteristic mentioned herein. The first nucleic acids may have any of the characteristics and properties of the second set of nucleic acids mentioned herein. The first set of nucleic acids is normally derived from a sample from the individuals which has undergone treatment and processing as described herein, particularly the EpiSwitch™ cross-linking and cleaving steps. Typically the first set of nucleic acids represents all or at least 80% or 50% of the chromosome interactions present in the samples taken from the individuals.

Typically, the first set of nucleic acids represents a smaller population of chromosome interactions across the loci or genes represented by the second set of nucleic acids in comparison to the chromosome interactions represented by second set of nucleic acids, i.e. the second set of nucleic acids is representing a background or index set of interactions in a defined set of loci or genes.

Nucleic Acids

Nucleic acids described herein may in the form of a library of nucleic acids which comprises at least 200, at least 500, at least 1,000, at least 5,000 or at least 10,000 different nucleic acids, up to for example up to 100,000 or 500,000 different nucleic acids as disclosed herein, such as the 'first' or 'second' set of nucleic acids. The library may be in the form of the nucleic acids bound to an array, for example in a manner which allows them to hybridise to complementary sequences.

Hybridisation

The invention requires a means for allowing wholly or partially complementary nucleic acid sequences from the first set of nucleic acids and the second set of nucleic acids to hybridise. In one embodiment all of the first set of nucleic acids is contacted with all of the second set of nucleic acids in a single assay, i.e. in a single hybridisation step. However any suitable assay can be used. In the embodiments described herein it is to be understood that binding of nucleic acids may be specific binding, typically by Watson-Crick base pairing (hybridising) between fully or partially complementary sequences.

Labelled Nucleic Acids and Pattern of Hybridisation

The nucleic acids mentioned herein may be labelled, for example using a detectable label, preferably using an independent label such as a fluorophore (fluorescent molecule) or radioactive label which assists detection of successful hybridisation. Certain labels can be detected under UV light. The pattern of hybridisation, for example on an array described herein, represents differences in epigenetic chromosome interactions between the two subgroups, and thus provides a method of comparing epigenetic chromosome interactions and determination of which epigenetic chromosome interactions are specific to a subgroup in the population of the present invention.

The term 'pattern of hybridisation' broadly covers the presence and absence of hybridisation between the first and second set of nucleic acids, i.e. which specific nucleic acids from the first set hybridise to which specific nucleic acids from the second set, and so it not limited to any particular assay or technique, or the need to have a surface or array on which a 'pattern' can be detected.

Selecting a Subgroup with Particular System Characteristics

The invention provides a method which comprises detecting the presence or absence of chromosome interactions, typically 1 to 5, or 5 to 20 or 5 to 500 such interactions, preferably 10 to 20 or 20 to 300 or 50 to 100 interactions, in order to determine the presence or absence of a characteristic in an individual. Preferably the chromosome interactions are those in any of the genes mentioned herein. In one embodiment the chromosome interactions which are typed are those represented by the nucleic acids in any one or more of the relevant Tables disclosed herein.

Preferably, the presence or absence of any of the chromosome interactions within any of the relevant genes mentioned herein are detected, for example in at least 1, 2, 3, 4, 5, 6, 10, 14, 15, up to all, of the genes mentioned in any table. Preferably the presence or absence of chromosome interactions represented by any specific primer and/or probe sequence disclosed herein is determined in the method. Typically the presence of one or more, such as 3, 5, 7 or 10 chromosome interactions represented by any specific primer and/or probe sequence disclosed herein and the absence of one or more, such as 3, 5, 7 or 10 chromosome interactions represented by any specific primer and/or probe sequence disclosed herein are determined in the method. These numbers of genes or chromosome interactions can be used in any of the different embodiments mentioned herein.

Specific Conditions

The method of the invention can be used to detect the presence of any of the specific conditions or characteristics mentioned herein, and preferably is used to detect likelihood of developing and/or predisposition to a neurodegenerative disease or condition, preferably a dementia such as Alzheimer's disease, mild cognitive impairment, vascular dementia, dementia with Lewy bodies, frontotemporal dementia, or more preferably Alzheimer's disease, most preferably beta-amyloid aggregate induced Alzheimer's disease.

Preferably, the presence and/or absence of any of the chromosome interactions within any of the relevant genes mentioned in the tables are detected. For example in at least 1, 3, 5, 10, 14, 15, or 20, or 30, or 42 of the genes mentioned in any one of the tables. Preferably the presence and/or absence of chromosome interactions represented by the probes sequences in the tables is determined in the method. These numbers of genes or chromosome interactions can be used in any of the different embodiments mentioned herein.

The Individual that is Tested

The individual to be tested may or may not have any symptoms of any condition or characteristic mentioned herein. The individual may be at risk of any such condition or characteristic. The individual is preferably a mammal, such as a primate, human, non-human mammal or rodent. The individual may be male or female. The individual may be 30 years old or older. The individual may be 29 years old or younger.

Preferred Gene Regions, Loci, Genes and Chromosome Interactions

For all aspects of the invention preferred gene regions (for example defined by specific position numbers), loci, genes and chromosome interactions are mentioned herein. Typically in the methods of the invention chromosome interactions are detected from at least 1, 3, 5, 10, 15 20, 30 or 42 of the relevant genes listed in the tables. Preferably the presence or absence of at least 1, 3, 5, 10, 15, 20, or 30 or 42 of the relevant specific chromosome interactions represented by the probe sequences in any one of the tables herein is detected. Preferably the presence or absence of at least 1, 3, 5, 10, 15, 20, or 30 or 42 of the relevant specific chromosome interactions represented by the primer sequences in any of the tables, for example 13, 14, 20, 30 or 42 are detected. In one embodiment no other chromosome interactions are detected.

The region may be upstream or downstream of any of the genes mentioned herein, for example 50 kb upstream or 20 kb downstream, for example from the coding sequence.

In one embodiment the chromosome interactions which are detected are present at any of the positions or in any of the regions (including the 4 kb region) shown in the tables. In the case where ligated products are detected in the method then sequence shown in any of the probe sequences in any of the tables may be detected. Thus typically sequence from both regions of the probe (i.e. from both sites of the chromosome interaction) could be detected, preferably including the junction sequence. In preferred embodiments probes are used in the method which comprise or consist of the same or complementary sequence to a probe shown in any table. In some embodiments probes are used which comprise sequence which is homologous to any of the probe sequences shown in the tables. In the case where ligated products are detected in the method by PCR then sequence shown in any of the probe sequences in any of the tables may be detected. Primers may detect or may be designed to hybridise within the probe locations and associated regions described in the tables. In preferred embodiments primer pairs are used in the method which comprise or consist of the same or complementary sequence to primer pairs shown in any table. In some embodiments primers are used which comprise sequence which is homologous to and/or a fragment of any of the primer sequences shown in the tables.

Particular combinations of chromosome interactions can be detected (i.e. determining the presence of absence of), which typically represent all of the interactions disclosed in a table herein or a selection from a table (such as any such selection defined herein). As mentioned herein particular numbers of interactions can be selected from individual tables. In one embodiment at least 10%, 20%, 30%, 50%, 70% or 90% of the interactions disclosed in any table (including table 3) are detected.

In one embodiment the presence or absence of at least 1, 3, 5, 6, 7, 8, 9, 10, 11, 12, 13, 14, 15, 20 of the relevant specific chromosome interactions represented by the smallest 50% of q-values (i.e. closest to 0) shown in table 3 are detected In one embodiment the presence of at least 1, 3, 5, 6, 7, 8, 9, 10 of the relevant specific chromosome interactions represented by the smallest 50% of q-values shown in table 3 are detected where presence of the interaction is associated with Alzheimer's disease and/or the absence of at least 1, 3, 5, 6, 7, 8, 9, 10 of the specific chromosome interactions represented by the smallest 50% of q-values shown in table 3 is detected wherein the absence of the interaction is associated with Alzheimer's disease.

In one embodiment any or all of the interactions shown in table 3 with a q-value of 0 to 0.003 may be detected. In another embodiment any or all of the interactions shown in table 3 with a q-value of 0.003 to 0.006 may be detected. In another embodiment any or all of the interactions shown in table 3 with a q-value of 0.006 to 0.01 may be detected.

In one embodiment any or all of the interactions represented by SEQ ID NO's 1 to 10 are detected. The method may be one in which any or all of the interactions represented by SEQ ID NO's 11 to 20 are detected. The method may be one in which any or all of the interactions represented by SEQ ID NO's 21 to 30 are detected. The method may be one in which any or all of the interactions represented by SEQ ID NO's 31 to 42 are detected.

The interactions which are detected may correspond to presence or absence of a particular characteristic, for example as defined herein, such as in any table herein. If a combination of interactions are detected then they may all correspond with presence of the characteristic or they may all correspond to absence of the characteristic. In one embodiment the combination of interactions which is detected corresponds to at least 2, 5 or 10 interactions which relate to presence of the characteristic and at least 2, 5 or 10 other interactions that relate to absence of the characteristic.

In one embodiment of the method any of the specific interactions disclosed herein or any of the specific selections disclosed herein are not detected in the method. Thus the method may be one in which the interactions represented by SEQ ID NO's 1 to 10 are not detected. The method may be one in which the interactions represented by SEQ ID NO's 11 to 20 are not detected. The method may be one in which the interactions represented by SEQ ID NO's 21 to 30 are not detected. The method may be one in which the interactions represented by SEQ ID NO's 31 to 42 are not detected.

Tables Provided Herein

The tables herein either show probe (Episwitch™ marker) data or gene data representing chromosome interactions present in a condition (the first mentioned group) and absent in a control group, or absent in a condition and present in the control group. The probe sequences show sequence which can be used to detect a ligated product generated from both sites of gene regions that have come together in chromosome interactions, i.e. the probe will comprise sequence which is complementary to sequence in the ligated product. The first two sets of Start-End positions (A) show probe positions, and the second two sets of Start-End positions (B) show the relevant 4 kb region (Table 2b).

The gene table data shows genes where a relevant chromosome interaction has been found to occur.

Table 3 shows the q-value calculated for each of the named probes and sets of primers. The q-value of a test measures the proportion of false positives incurred (called the false discovery rate) when that particular test is called significant. The probe may represent a marker which is prevalent in the subgroup with a condition, or a marker which is absent in the subgroup with a condition but present in the control subgroup.

Table 4 lists preferred markers for use in the method of the invention. These markers may be detected for example using the primers associated with the marker directly in an amplification reaction or by using the probe sequence. AD-P markers are present in Alzheimer's patients but not in control patients. AD-N markers are prevalent in control patients but not in Alzheimer's patients.

The probes are designed to be 30 bp away from the Taq1 site. In case of PCR, PCR primers are also designed to detect ligated product but their locations from the Taq1 site vary.

Probe Locations:
Start 1-30 bases upstream of TaqI site on fragment 1
End 1—TaqI restriction site on fragment 1
Start 2—TaqI restriction site on fragment 2
End 2-30 bases downstream of TaqI site on fragment 2
4 kb Sequence Location:
Start 1-4000 bases upstream of TaqI site on fragment 1
End 1—TaqI restriction site on fragment 1
Start 2—TaqI restriction site on fragment 2
End 2-4000 bases downstream of TaqI site on fragment 2

Preferred Embodiments for Sample Preparation and Chromosome Interaction Detection Methods of preparing samples and detecting chromosome conformations are described herein. Optimised (non-conventional) versions of these methods can be used, for example as described in this section.

Typically the sample will contain at least $2 \times 10^5$ cells. The sample may contain up to $5 \times 10^5$ cells. In one embodiment, the sample will contain $2 \times 10^5$ to $5.5 \times 10^5$ cells Cross-linking of epigenetic chromosomal interactions present at the chromosomal locus is described herein. This may be performed before cell lysis takes place. Cell lysis may be performed for 3 to 7 minutes, such as 4 to 6 or about 5 minutes. In some embodiments, cell lysis is performed for at least 5 minutes and for less than 10 minutes.

Digesting DNA with a restriction enzyme is described herein. Typically, DNA restriction is performed at about 55° C. to about 70° C., such as for about 65° C., for a period of about 10 to 30 minutes, such as about 20 minutes.

Preferably a frequent cutter restriction enzyme is used which results in fragments of ligated DNA with an average fragment size up to 4000 base pair. Optionally the restriction enzyme results in fragments of ligated DNA have an average fragment size of about 200 to 300 base pairs, such as about 256 base pairs. In one embodiment, the typical fragment size is from 200 base pairs to 4,000 base pairs, such as 400 to 2,000 or 500 to 1,000 base pairs.

In one embodiment of the EpiSwitch™ method a DNA precipitation step is not performed between the DNA restriction digest step and the DNA ligation step.

DNA ligation is described herein. Typically the DNA ligation is performed for 5 to 30 minutes, such as about 10 minutes.

The protein in the sample may be digested enzymatically, for example using a proteinase, optionally Proteinase K. The protein may be enzymatically digested for a period of about 30 minutes to 1 hour, for example for about 45 minutes. In one embodiment after digestion of the protein, for example Proteinase K digestion, there is no cross-link reversal or phenol DNA extraction step.

In one embodiment PCR detection is capable of detecting a single copy of the ligated nucleic acid, preferably with a binary read-out for presence/absence of the ligated nucleic acid.

Methods and Uses of the Invention

The method of the invention can be described in different ways. It can be described as a method of making a ligated nucleic acid comprising (i) in vitro cross-linking of chromosome regions which have come together in a chromosome interaction; (ii) subjecting said cross-linked DNA to cutting or restriction digestion cleavage; and (iii) ligating said cross-linked cleaved DNA ends to form a ligated nucleic acid, wherein detection of the ligated nucleic acid may be used to determine the chromosome state at a locus, and wherein preferably:

the locus may be any of the loci, regions or genes mentioned herein, and/or wherein the chromosomal interaction may be any of the chromosome interactions mentioned herein or corresponding to any of the probes disclosed in the tables, and/or wherein the ligated product may have or comprise (i) sequence which is the same as or homologous to any of the probe sequences disclosed herein; or (ii) sequence which is complementary to (ii).

Homologues and Fragments

In any embodiment homologues and/or fragments of specific sequences can be used instead, and optionally they will have the same binding characteristics as the original sequence.

Homologues of polynucleotide/nucleic acid (e.g. DNA) sequences are referred to herein. Such homologues typically have at least 70% homology, preferably at least 80%, at least 85%, at least 90%, at least 95%, at least 97%, at least 98% or at least 99% homology, for example over a region of at least 10, 15, 20, 30, 100 or more contiguous nucleotides, or across the portion of the nucleic acid which is from the region of the chromosome involved in the chromosome interaction. The homology may be calculated on the basis of nucleotide identity (sometimes referred to as "hard homology").

Therefore, in a particular embodiment, homologues of polynucleotide/nucleic acid (e.g. DNA) sequences are referred to herein by reference to % sequence identity. Typically such homologues have at least 70% sequence identity, preferably at least 80%, at least 85%, at least 90%, at least 95%, at least 97%, at least 98% or at least 99% sequence identity, for example over a region of at least 10, 15, 20, 30, 100 or more contiguous nucleotides, or across the portion of the nucleic acid which is from the region of the chromosome involved in the chromosome interaction.

For example the UWGCG Package provides the BEST-FIT program which can be used to calculate homology and/or % sequence identity (for example used on its default settings) (Devereux et al (1984) Nucleic Acids Research 12, p 387-395). The PILEUP and BLAST algorithms can be used to calculate homology and/or % sequence identity and/or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W5 T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by 1, 2, 3, 4 or more bases, such as less than 10, 15 or 20 bases (which may be substitutions, deletions or insertions of nucleotides). These changes may be measured across any of the regions mentioned above in relation to calculating homology and/or % sequence identity.

Fragments or portions of sequences typically comprise at least 70%, such as at least 80%, 90% or 100% of the original sequence, and typically are at least 10, 20 or 30 base pairs in length.

Arrays

The second set of nucleic acids may be bound to an array, and in one embodiment there are at least 15,000, 45,000, 100,000 or 250,000 different second nucleic acids bound to the array, which preferably represent at least 300, 900, 2000 or 5000 loci. In one embodiment one, or more, or all of the different populations of second nucleic acids are bound to more than one distinct region of the array, in effect repeated on the array allowing for error detection. The array may be based on an Agilent SurePrint G3 Custom CGH microarray platform. Detection of binding of first nucleic acids to the array may be performed by a dual colour system.

Therapeutic Agents

Therapeutic agents are mentioned herein. The invention provides such agents for use in preventing or treating the relevant condition. This may comprise administering to an individual in need a therapeutically effective amount of the agent. The invention provides use of the agent in the manufacture of a medicament to prevent or treat the disease. The methods of the invention may be used to select an individual for treatment. The methods of the invention, and in particular the method for carrying out a companion epigenetic test, may include a treatment step where a person identified by the method may then be administered with an agent that prevents or treats the relevant condition.

The formulation of the agent will depend upon the nature of the agent. The agent will be provided in the form of a pharmaceutical composition containing the agent and a pharmaceutically acceptable carrier or diluent. Suitable carriers and diluents include isotonic saline solutions, for example phosphate-buffered saline. Typical oral dosage compositions include tablets, capsules, liquid solutions and liquid suspensions. The agent may be formulated for parenteral, intravenous, intramuscular, subcutaneous, transdermal or oral administration.

The dose of an agent may be determined according to various parameters, especially according to the substance used; the age, weight and condition of the individual to be treated; the route of administration; and the required regimen. A physician will be able to determine the required route of administration and dosage for any particular agent. A suitable dose may however be from 0.1 to 100 mg/kg body weight such as 1 to 40 mg/kg body weight, for example, to be taken from 1 to 3 times daily.

Forms of the Substance Mentioned Herein

Any of the substances, such as nucleic acids or therapeutic agents, mentioned herein may be in purified or isolated form. The may be in a form which is different from that found in nature, for example they may be present in combination with other substance with which they do not occur in nature. The nucleic acids (including portions of sequences defined herein) may have sequences which are different to those found in nature, for example having at least 1, 2, 3, 4 or more nucleotide changes in the sequence as described in the section on homology. The nucleic acids may have heterologous sequence at the 5' or 3' end. The nucleic acids may be chemically different from those found in nature, for example they may be modified in some way, but preferably are still capable of Watson-Crick base pairing. Where appropriate the nucleic acids will be provided in double stranded or single stranded form. The invention provides all of the specific nucleic acid sequences mentioned herein in single or double stranded form, and thus includes the complementary strand to any sequence which is disclosed.

The invention also provides a kit for carrying out any process of the invention, including detection of a chromosomal interaction associated with a particular subgroup. Such a kit can include a specific binding agent capable of detecting the relevant chromosomal interaction, such as agents capable of detecting a ligated nucleic acid generated by processes of the invention. Preferred agents present in the kit include probes capable of hybridising to the ligated nucleic acid or primer pairs, for example as described herein, capable of amplifying the ligated nucleic acid in a PCR reaction.

The invention also provides a device that is capable of detecting the relevant chromosome interactions. The device preferably comprises any specific binding agents, probe or primer pair capable of detecting the chromosome interaction, such as any such agent, probe or primer pair described herein.

Preferred therapeutic agents for use in the invention for specific stated condition A. Treatment for Mild to moderate Alzheimer's Disease (MMAD)

Cholinesterase inhibitors may be used to treat mild to moderate Alzheimer's disease. Medications that may be used include galantamine, rivastigmine and donepezil.

B. Treatment for Moderate to Severe Alzheimer's

An N-methyl D-aspartate antagonist may be prescribed to treat moderate to severe Alzheimer's disease, e.g. Memantine is an NMDA antagonist approved by the FDA for treatment of Alzheimer's disease.

NMDA antagonists may be used in combination with cholinesterase inhibitors. For example, Aricept and Namzaric, a combination of memantine and donepezil are approved by the FDA for treatment of moderate to severe Alzheimer's disease.

The skilled person will be able to identify in the art appropriate therapeutic agents for other neurodegenerative conditions.

Specific Embodiments

The EpiSwitch™ platform technology detects epigenetic regulatory signatures of regulatory changes between normal and abnormal conditions at loci. The EpiSwitch™ platform identifies and monitors the fundamental epigenetic level of gene regulation associated with regulatory high order structures of human chromosomes also known as chromosome conformation signatures. Chromosome signatures are a distinct primary step in a cascade of gene deregulation. They are high order biomarkers with a unique set of advantages against biomarker platforms that utilize late epigenetic and gene expression biomarkers, such as DNA methylation and RNA profiling.

EpiSwitch™ Array Assay

The custom EpiSwitch™ array-screening platforms come in 4 densities of, 15K, 45K, 100K, and 250K unique chromosome conformations, each chimeric fragment is repeated on the arrays 4 times, making the effective densities 60K, 180K, 400K and 1 Million respectively.

Custom Designed EpiSwitch™ Arrays

The 15K EpiSwitch™ array can screen the whole genome including around 300 loci interrogated with the EpiSwitch™ Biomarker discovery technology. The EpiSwitch™ array is built on the Agilent SurePrint G3 Custom CGH microarray platform; this technology offers 4 densities, 60K, 180K, 400K and 1 Million probes. The density per array is reduced to 15K, 45K, 100K and 250K as each EpiSwitch™ probe is presented as a quadruplicate, thus allowing for statistical evaluation of the reproducibility. The average number of potential EpiSwitch™ markers interrogated per genetic loci is 50; as such the numbers of loci that can be investigated are 300, 900, 2000, and 5000.

EpiSwitch™ Custom Array Pipeline

The EpiSwitch™ array is a dual colour system with one set of samples, after EpiSwitch™ library generation, labelled in Cy5 and the other of sample (controls) to be compared/analyzed labelled in Cy3. The arrays are scanned using the Agilent SureScan Scanner and the resultant features extracted using the Agilent Feature Extraction software. The data is then processed using the EpiSwitch™ array processing scripts in R. The arrays are processed using standard dual colour packages in Bioconductor in R: Limma*. The normalisation of the arrays is done using the normalised within Arrays function in Limma* and this is done to the on chip Agilent positive controls and EpiSwitch™ positive controls. The data is filtered based on the Agilent Flag calls, the Agilent control probes are removed and the technical replicate probes are averaged, in order for them to be analysed using Limma*. The probes are modelled based on their difference between the 2 scenarios being compared and then corrected by using False Discovery Rate. Probes with Coefficient of Variation (CV)<=30% that are <=−1.1 or =>1.1 and pass the p<=0.1 FDR p-value are used for further screening. To reduce the probe set further Multiple Factor Analysis is performed using the FactorMineR package in R.

* Note: LIMMA is Linear Models and Empirical Bayes Processes for Assessing Differential Expression in Microarray Experiments. Limma is a R package for the analysis of gene expression data arising from microarray or RNA-Seq.

The pool of probes is initially selected based on adjusted p-value, FC and CV<30% (arbitrary cut off point) parameters for final picking. Further analyses and the final list are drawn based only on the first two parameters (adj. p-value; FC).

Statistical Pipeline

EpiSwitch™ screening arrays are processed using the EpiSwitch™ Analytical Package in R in order to select high value EpiSwitch™ markers for translation on to the EpiSwitch™ PCR platform.

Step 1. Probes are selected based on their corrected p-value (False Discovery Rate, FDR), which is the product of a modified linear regression model. Probes below p-value <=0.1 are selected and then further reduced by their Epigenetic ratio (ER), probes ER have to be <=−1.1 or =>1.1 in order to be selected for further analysis. The last filter is a coefficient of variation (CV), probes have to be below <=0.3.

Step 2. The top 40 markers from the statistical lists are selected based on their ER for selection as markers for PCR translation. The top 20 markers with the highest negative ER load and the top 20 markers with the highest positive ER load form the list.

Step 3. The resultant markers from step 1, the statistically significant probes form the bases of enrichment analysis using hypergeometric enrichment (HE). This analysis enables marker reduction from the significant probe list, and along with the markers from step 2 forms the list of probes translated on to the EpiSwitch™ PCR platform.

The statistical probes are processed by HE to determine which genetic locations have an enrichment of statistically significant probes, indicating which genetic locations are hubs of epigenetic difference.

The most significant enriched loci based on a corrected p-value are selected for probe list generation. Genetic locations below p-value of 0.3 or 0.2 are selected. The statistical probes mapping to these genetic locations, with the markers from step 2, form the high value markers for EpiSwitch™ PCR translation.

Array Design and Processing
Array Design
1. Genetic loci are processed using the SII software (currently v3.2) to:
   a. Pull out the sequence of the genome at these specific genetic loci (gene sequence with 50 kb upstream and 20 kb downstream)
   b. Define the probability that a sequence within this region is involved in CC's
   c. Cut the sequence using a specific RE
   d. Determine which restriction fragments are likely to interact in a certain orientation
   e. Rank the likelihood of different CC's interacting together.
2. Determine array size and therefore number of probe positions available (x)
3. Pull out x/4 interactions.
4. For each interaction define sequence of 30 bp to restriction site from part 1 and 30 bp to restriction site of part 2. Check those regions aren't repeats, if so exclude and take next interaction down on the list. Join both 30 bp to define probe.
5. Create list of x/4 probes plus defined control probes and replicate 4 times to create list to be created on array
6. Upload list of probes onto Agilent Sure design website for custom CGH array.
7. Use probe group to design Agilent custom CGH array.

Array Processing
1. Process samples using EpiSwitch™ SOP for template production.
2. Clean up with ethanol precipitation by array processing laboratory.
3. Process samples as per Agilent SureTag complete DNA labelling kit—Agilent Oligonucleotide Array-based CGH for Genomic DNA Analysis Enzymatic labelling for Blood, Cells or Tissues
4. Scan using Agilent C Scanner using Agilent feature extraction software.

PUBLICATIONS

The contents of all publications mentioned herein are incorporated by reference into the present specification and may be used to further define the features relevant to the invention.

Examples

The inventors characterised the epigenetic profile of patients with a neurodegenerative condition basing on looking at AD (Alzheimer's disease) positive patients and age matched AD negative controls. Details of genes where AD markers have been identified are shown in Table 1, along with the associated probe sequences and locations (Table 2). The proprietary EpiSwitch™ extraction process was performed on samples using 50 µl of blood per extraction reaction. Briefly, the samples were fixed with formaldehyde, incubated for 15 minutes and quenched with glycine. The samples were lysed and nuclei purified using density cushion centrifugation. Proximity ligation was performed with the restriction enzyme TaqI and T4 DNA Ligase. For each extraction the protein and RNA content was removed via Proteinase K.

Figure 2:
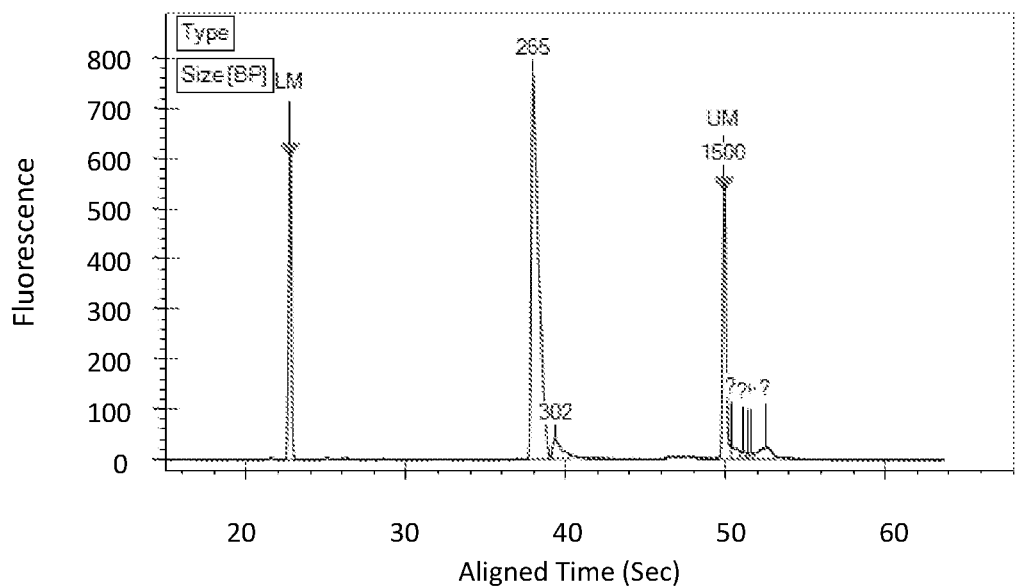
FIG. 2 is an example of (A) the electropherogram for a single sample, and (B) a virtual gel image of generated using the LabChip GX system comparing a number of samples, for a marker prevalent in Alzheimer's disease patients compared with the Control samples. The analysis was performed using 50 µl of blood per sample. In panel (B) the label at the top of each column represents the sample type (ALZ: Alzheimer's patient; CTL: Control patient) and the PCR primers used. Primer Pair: OB140_061.063; Marker: 10_14270092_14271521_14310504_14315691_RR; q value for this marker: 0.006191144.
Figure 2:
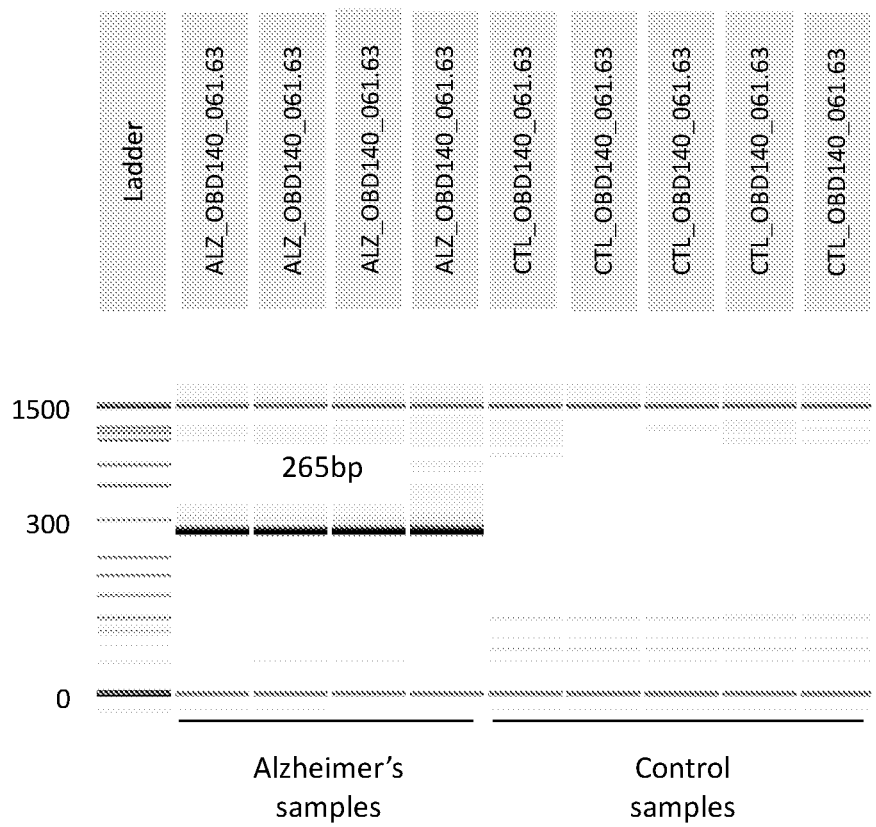
Figure 3:
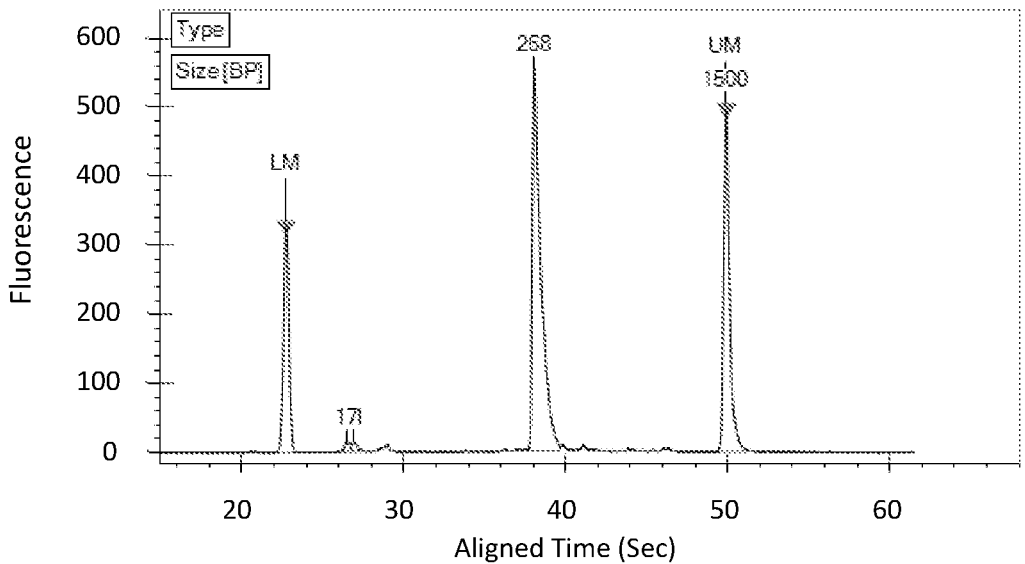
FIG. 3 is an example of (A) the electropherogram for a single sample, and (B) a virtual gel image of generated using the LabChip GX system comparing a number of samples, for a marker prevalent in Control samples compared with Alzheimer's disease patients. The analysis was performed using 50 µl of blood per sample. In panel (B) the label at the top of each column represents the sample type (ALZ: Alzheimer's patient; CTL: Control patient) and the PCR primers used. Primer Pair: OB140_005.007; Marker: 8_3184876_3186946_3214817_3221560_FR; q value for this marker is 0.005343515.
Figure 3:
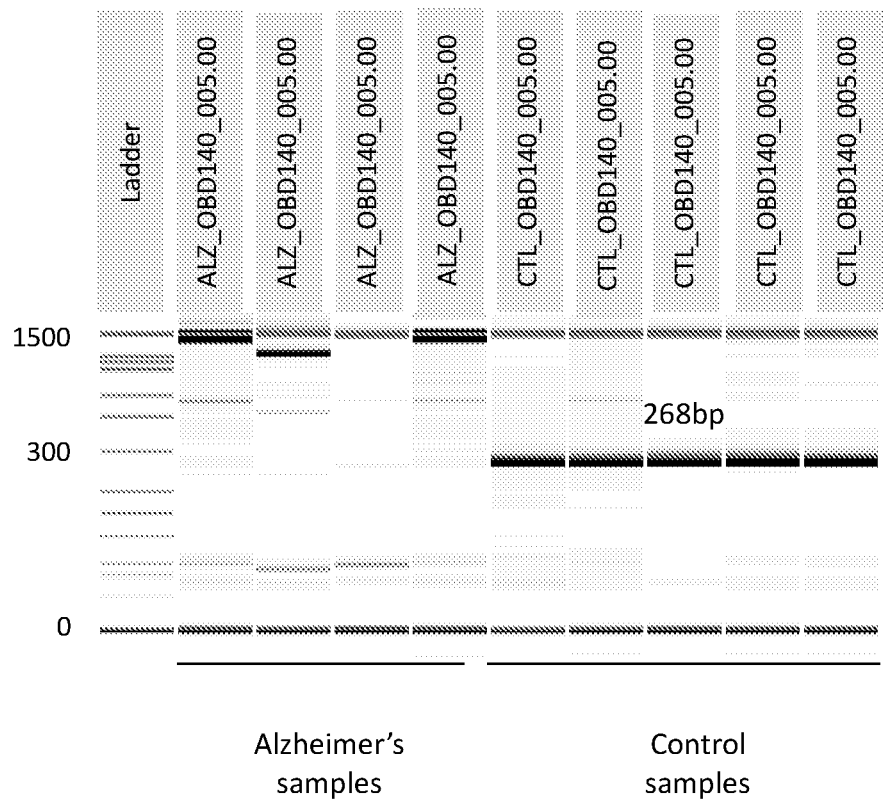

Nested PCR was performed using 13 µl of the sample dilution series as template. The LabChip GX Touch HT (Perkin Elmer) high throughput gel electrophoresis system was used to analyse the PCR products. The LabChip system from Perkin Elmer performs gel electrophoresis inside a "Lab on a chip" using capillary electrophoresis. The detection of PCR products is through a DNA Dye\laser excitation system and sizing and concentration measurements calculated against a known standard ladder. Each ladder and Sample tested has a lower and upper marker compound mixed in before the capillary gel electrophoresis is performed to allow correct alignment against the ladder. The output of the LabChip GX system is in the form of an electropherogram of Relative fluorescent units on the Y axis and time on the X axis (e.g. FIGS. 2 and 3). The Perkin Elmer software creates a virtual gel image of the electropherogram to represent a traditional gel image. The size and concentration of each DNA peak detected is quantified and presents on the electropherogram/virtual gel image and an exportable table.

The PCR reactions that contain peaks that are identified as the correct size (those that match expected sizes based on possible 3C interactions) are recorded as a "1" to indicate the detection of the product whereas a sample were the product is not detected is recorded as a "0". This read out provides the binary read out for the EpiSwitch nested PCR platform. Multiple sized peaks may be expected for each primer combination due to alternative TaqI sites so all predicted peak sizes are analysed.

Patient Diagnosis

Samples with ligated DNA derived from 5 Alzheimer's patients (severe to moderate dementia), and 5 age-matched controls were subjected to PCR assay using the primers described in table 3.

Table 3 shows EpiSwitch™ probes for AD versus patients from the control group (AD-N), along with the q-value for the marker and whether the marker is prevalent in the Alzheimer's patient cohort or in the control cohort.

Table 4 gives details of 14 preferred markers for AD, including whether they are expected to be prevalent in subjects with Alzheimer's disease or absent in in subjects with Alzheimer's disease.

Samples

The blood samples yielding the current data all came from Caucasians in Moscow, Russia.

TABLE 1

| Genes | Full Name/Alias | Activity |
| --- | --- | --- |
| ABL1 | ABL Proto-Oncogene 1, Non-Receptor Tyrosine Kinase | magnesium ion binding and SH3 domain binding |
| AGAP1 | ArfGAP With GTPase Domain, Ankyrin Repeat And PH Domain 1 | membrane trafficking, cytoskeleton dynamics |

TABLE 1-continued

| Genes | Full Name/Alias | Activity |
|---|---|---|
| ANKS1B | Ankyrin Repeat And Sterile Alpha Motif Domain Containing 1B | ephrin receptor binding |
| CAMTA1 | Calmodulin Binding Transcription Activator 1 | Protein Coding gene |
| CHN2 | Chimerin 2 | cell proliferation and migration |
| CNTNAP2 | Contactin Associated Protein-Like 2 | cell adhesion |
| CPNE4 | Copine 4 | membrane trafficking, mitogenesis and development |
| CSMD1 | CUB And Sushi Multiple Domains 1 | Protein Coding gene |
| CSMD2 | CUB And Sushi Multiple Domains 2 | Protein Coding gene |
| DIP2C | FYN Proto-Oncogene, Src Family Tyrosine Kinase | control of cell growth |
| DLG2 | Discs Large MAGUK Scaffold Protein 2 | membrane-associated guanylate kinase |
| DOCK4 | Dedicator Of Cytokinesis 4 | regulation of adherens junctions between cells |
| EPHB1 | EPH Receptor B1 | developmental processes, nervous system |
| FRMD4A | FERM Domain Containing 4A | regulates epithelial cell polarity |
| FYN | FYN Proto-Oncogene, Src Family Tyrosine Kinase | control of cell growth |
| GRIN2B | Glutamate Ionotropic Receptor NMDA Type Subunit 2B | ionotropic glutamate receptor |
| HECW1 | HECT, C2 And WW Domain Containing E3 Ubiquitin Protein Ligase 1 | ubiquitin protein ligase activity |
| NAV2 | Neuron Navigator 2 | heparin binding and helicase activity |
| NRG1 | Neuregulin 1 | cell-cell signaling, growth and development |
| NTM | Neurotrimin | protein binding |
| NTRK3 | Neurotrophic Receptor Tyrosine Kinase 3 | cell differentiation and development of proprioceptive neurons |
| PSD3 | Pleckstrin And Sec7 Domain Containing 3 | phospholipid binding and ARF guanyl-nucleotide exchange factor activity |
| PTPRD | Protein Tyrosine Phosphatase, Receptor Type D | processes including cell growth, differentiation, mitotic cycle, and oncogenic transformation |
| PTPRG | Protein Tyrosine Phosphatase, Receptor Type G | regulates cell growth, differentiation and mitotic cycle |
| SMYD3 | SET And MYND Domain Containing 3 | functions in RNA polymerase II complexes |
| SND1 | Staphylococcal Nuclease And Tudor Domain Containing 1 | transcriptional co-activator |
| SORCS3 | Sortilin Related VPS10 Domain Containing Receptor 3 | member of the vacuolar protein sorting 10 receptor family |
| SPOCK1 | Sparc/Osteonectin, Cwcv And Kazal-Like Domains Proteoglycan (Testican) 1 | calcium ion binding and cysteine-type endopeptidase inhibitor activity |
| SRGAP3 | SLIT-ROBO Rho GTPase Activating Protein 3 | GTPase activator activity and Rac GTPase binding |
| TCF7L2 | Transcription Factor 7 Like 2 | transcription factor that plays a key role in the Wnt signaling pathway |
| TJP1 | Tight Junction Protein 1 | signal transduction at cell-cell junctions |
| TRAPPC9 | Trafficking Protein Particle Complex 9 | activator of NF-kappa-B through increased phosphorylation of the IKK complex |
| VPS13B | Vacuolar Protein Sorting 13 Homolog B | vesicle-mediated transport and sorting of proteins |
| ZNF536 | Zinc Finger Protein 536 | retinoic acid-responsive element binding |

TABLE 2 a Gene locus/Name and 60-mer Probe Sequence with associated SeqID.

| SEQ ID* | Gene Locus/Name | 60 mer |
|---|---|---|
| 1 | NRG1 | GGCAGGCAGATTACTTGAGGTTAGGAATTCGATGCCGATAGAGTAAAAAGCATTCTCTGT |
| 2 | PSD3 | TTTATTAAAAATCACTGAATTATATGGTTCGATGAAAAATATTCTTTAGATCTAAGACCT |
| 3 | TRAPPC9 | AATGTAATTGATCTGGGACTCTGCCACCTCGAAAAGAGCTGCCCTCCCCTGGCTGCTGTG |
| 4 | ANKS1B | CATACACAAAGCAATCTGAGATGGATTATCGAAGTAAAAATTTTTACAGATTCTCTAAGT |
| 5 | EPHB1 | GGCAGTTGGATCATTTGAGTCCAAGAGTTCGACACTCTCATTCTGATTCTGTTTGAACCC |
| 6 | ABL1 | AGAGGGGCCAAGTGTGACTCTCAGGTTTTCGACTCCCTTAGAAACATGCAGTTGTTGTTT |
| 7 | CPNE4 | TTCTAGGGTGTTACATTTCAAAGAATTTTCGACTTGAACTTCTGCCTCTCTATTTGTATC |
| 8 | GRIN2B | AAGACTGTCTCCCAGATATCTTGCTCATTCGAAGACTGTCTTGCTAGAAAGAATATTCTT |
| 9 | PSD3 | TTTATTAAAAATCACTGAATTATATGGTTCGATTCACAGTCTCTTCATTTGATCAGAATC |
| 10 | VPS13B | AGCAGGGTGTGGTGATGAAGAGGCTGACTCGATAAACAGCAAAGTTCCTTTCCCAGCCTA |
| 11 | PSD3 | TTTATTAAAAATCACTGAATTATATGGTTCGATTTCCAGTACAACTCTATGAAGAAGTTA |

TABLE 2-continued a Gene locus/Name and 60-mer Probe Sequence with associated SeqID.

| SEQ ID* | Gene Locus/ Name | 60 mer |
|---|---|---|
| 12 | DLG2 | AAACAGATGTGAGATGATCAGATTTACATCGATAGTATTATACGTGGTCATTAGCCTCAG |
| 13 | NTRK3 | GCTGGGGGTCTCATCATTCTTCCCCTCCTCGACTCTTCTCTGTCACCCATTATTCAATCT |
| 14 | CSMD1 | GAAAAGACCCTTCAAGCAGATGGAGAGTTCGAGTCTTCCTAGCTCTGTGTCCTTGGGCAA |
| 15 | DOCK4 | CCATAAAGGAGGGCAATGGAAGAAGAGTCGACTATTTTATTTTTGTAGAGACGAGATC |
| 16 | CSMD1 | GAAAAGACCCTTCAAGCAGATGGAGAGTTCGATTACCTCAAACAAAGAGGAATAGCACTA |
| 17 | SPOCK1 | ATGACAAGTGAATGAAGCTGAATATGTATCGACTTCTCTCTGCCACCCCCAACTGTGAGC |
| 18 | SPOCK1 | GTAGTATGTAGTGGTTACAGCATGATCTTCGACTTCTCTCTGCCACCCCCAACTGTGAGC |
| 19 | NRG1 | GGCAGGCAGATTACTTGAGGTTAGGAATTCGATTCTGACTTAAGAGACATAAACAAGGAA |
| 20 | NAV2 | CCTCATTTACAAATGAGAAAACTAAGAGTCGAAAGAAAATATTCTTCTTTCCTGACCATT |
| 21 | SRGAP3 | GTGTGGCCTAATCAAGAACCAATCAGAGTCGAACTCATCATCCTCCCTCCCCGCCCCACC |
| 22 | SORCS3 | TGAATGAGTCACTTAATTTGAGTTTGTATCGACTCACTGTACTCCAGCCTGGCAACAGAG |
| 23 | HECW1 | TACCTTCTTTCAATCCGGATATTTTCAGTCGATGTAAGAGTAACATATATTGTTCAATAT |
| 24 | FRMD4A | GAAACAGGTGGGTCATGAGGTCAAGAGATCGATTTATTTATTTTTTCATTCATCTTCATA |
| 25 | NTM | ATTATTTTCCTTCTGCCTTAATCCTCTTTCGACGCTCCTCTTCCTGTATGCATGGTTTCT |
| 26 | SMYD3 | CTGACAAACCACTTAGCTTGTGTGATATTCGACTGGCTGACAAGTACCCCCAGACCAGAA |
| 27 | ZNF536 | ACACGATAAAAGCTTCAAAGAGAAAATGTCGATCTGGACTCTGCCTGCCCCTACTTCATC |
| 28 | PTPRG | GAAGATAAAAAGCTCAAAATGAATGAACTCGATGCCTGCCTCCCACCTTTCTGAGTTGAG |
| 29 | CSMD1 | GAAAAGACCCTTCAAGCAGATGGAGAGTTCGAAGGAAGCATTCAGCCATTATTCACTAAG |
| 30 | SORCS3 | TAGGTGGGTGGGTTACGAGGCCAGAAGATCGATACAAACTCAAATTAAGTGACTCATTCA |
| 31 | CSMD2 | CAAGTGCATTCCCATGTGGGACCTTCTTTCGAGCAGGGTAGTGAATGTTTGGGGTAGTTT |
| 32 | TCF7L2 | CAGGGTGCTGGAAAATGCCCACTTTGCCTCGAGCTTGCGTCACTGCACTCCAGCCTAGGC |
| 33 | SND1 | TTATACTACAGGGACTCTTTGATCTGGGTCGAAAAGGTGCACAAATGAAAAGGGTACCGC |
| 34 | CNTNAP2 | CTGGCAAGTCTCAGCTCTTTGCTAGTCATCGACTCCTTCCCTGTCCTGCTTCCATTGTTT |
| 35 | CAMTA1 | GCCTGCAGGATCCCTGGGCAAGCGTGCTTCGAGGCACCCCATCCCCATCCCCACTCTGTC |
| 36 | DIP2C | CTGTCAGTTACAGAGGAAGACTGCTGTGTCGACCTCCTCCTCCTGCCTCAGCTCCCAAGC |
| 37 | HECW1 | TACCTTCTTTCAATCCGGATATTTTCAGTCGATGTATATCCGTGAACTTTGGGGTAACAT |
| 38 | CHN2 | AGCAGGCAGATCACTTAAGGACAAGAGTTCGAAATCATTTCTGATGGAAGGAAAGGAAGA |
| 39 | AGAP1 | GAGCAGCTGCCCAGAATCTGTCTTGTCATCGACCCTCTGTGCCTCAGTTTCCTTATCCAG |
| 40 | TJP1 | GAGTAGTGGTGTCTTCTCAAGAGGAAAATCGATTACATATTAAGGAATTCTGGAAGATAC |
| 41 | PTPRD | TAACTAAGTGCAAATGTTCTACCAGCATTCGAGAATAAAATGTCCTTTGTAGCATGCTTT |
| 42 | FYN | CCAAATCCGAACCTCCTCTGTGAAGCATTCGAGTTGTTGCCACCCCACCCTCCTCAAACC |

TABLE 2b

Probe Name, location (A) and 4 kb associated region (B).

| Seq ID* | Table 2b. Probe name | | Chr | Start1 | End1 | Start2 | End2 |
|---|---|---|---|---|---|---|---|
| 1 | 8_31516198_31523606_31818711_31822095_RR | A | 8 | 31516200 | 31516229 | 31818713 | 31818742 |
| | | B | 8 | 31516200 | 31520199 | 31818713 | 31822712 |

TABLE 2b-continued

Probe Name, location (A) and 4 kb associated region (B).

| Seq ID* | Table 2b. Probe name | | Chr | Start1 | End1 | Start2 | End2 |
|---|---|---|---|---|---|---|---|
| 2 | 8_18627026_18630239_18802479_18805120_RR | A | 8 | 18627028 | 18627057 | 18802481 | 18802510 |
| | | B | 8 | 18627028 | 18631027 | 18802481 | 18806480 |
| 3 | 8_141055883_141058992_141086377_141087725_RR | A | 8 | 141055885 | 141055914 | 141086379 | 141086408 |
| | | B | 8 | 141055885 | 141059884 | 141086379 | 141090378 |
| 4 | 12_99829998_99832967_99923655_99925739_FR | A | 12 | 99832936 | 99832965 | 99923657 | 99923686 |
| | | B | 12 | 99828966 | 99832965 | 99923657 | 99927656 |
| 5 | 3_134760993_134763662_134867764_134877240_RR | A | 3 | 134760995 | 134761024 | 134867766 | 134867795 |
| | | B | 3 | 134760995 | 134764994 | 134867766 | 134871765 |
| 6 | 9_133594848_133596271_133727385_133729777_FF | A | 9 | 133596240 | 133596269 | 133729746 | 133729775 |
| | | B | 9 | 133592270 | 133596269 | 133725776 | 133729775 |
| 7 | 3_131505858_131513308_131747714_131750544_RF | A | 3 | 131505860 | 131505889 | 131750513 | 131750542 |
| | | B | 3 | 131505860 | 131509859 | 131746543 | 131750542 |
| 8 | 12_13876814_13882582_14175710_14178153_FR | A | 12 | 13882551 | 13882580 | 14175712 | 14175741 |
| | | B | 12 | 13878581 | 13882580 | 14175712 | 14179711 |
| 9 | 8_18627026_18630239_18683324_18685195_RR | A | 8 | 18627028 | 18627057 | 18683326 | 18683355 |
| | | B | 8 | 18627028 | 18631027 | 18683326 | 18687325 |
| 10 | 8_100791664_100796954_100828549_100846158_FF | A | 8 | 100796923 | 100796952 | 100846127 | 100846156 |
| | | B | 8 | 100792953 | 100796952 | 100842157 | 100846156 |
| 11 | 8_18627026_18630239_18789667_18794069_RR | A | 8 | 18627028 | 18627057 | 18789669 | 18789698 |
| | | B | 8 | 18627028 | 18631027 | 18789669 | 18793668 |
| 12 | 11_83262014_83266402_83456642_83461359_FF | A | 11 | 83266371 | 83266400 | 83461328 | 83461357 |
| | | B | 11 | 83262401 | 83266400 | 83457358 | 83461357 |
| 13 | 15_88561155_88565981_88737279_88740659_FR | A | 15 | 88565950 | 88565979 | 88737281 | 88737310 |
| | | B | 15 | 88561980 | 88565979 | 88737281 | 88741280 |
| 14 | 8_3184876_3186946_3214817_3221560_FR | A | 8 | 3186915 | 3186944 | 3214819 | 3214848 |
| | | B | 8 | 3182945 | 3186944 | 3214819 | 3218818 |
| 15 | 7_111502152_111504459_111764240_111773350_FR | A | 7 | 111504428 | 111504457 | 111764242 | 111764271 |
| | | B | 7 | 111500458 | 111504457 | 111764242 | 111768241 |
| 16 | 8_3161496_3163915_3184876_3186946_RF | A | 8 | 3161498 | 3161527 | 3186915 | 3186944 |
| | | B | 8 | 3161498 | 3165497 | 3182945 | 3186944 |
| 17 | 5_136390820_136396782_136690182_136694747_FR | A | 5 | 136396751 | 136396780 | 136690184 | 136690213 |
| | | B | 5 | 136392781 | 136396780 | 136690184 | 136694183 |
| 18 | 5_136613132_136616425_136690182_136694747_RR | A | 5 | 136613134 | 136613163 | 136690184 | 136690213 |
| | | B | 5 | 136613134 | 136617133 | 136690184 | 136694183 |
| 19 | 8_31516198_31523606_31643705_31652690_RR | A | 8 | 31516200 | 31516229 | 31643707 | 31643736 |
| | | B | 8 | 31516200 | 31520199 | 31643707 | 31647706 |
| 20 | 11_19756575_19766996_19853230_19857899_RR | A | 11 | 19756577 | 19756606 | 19853232 | 19853261 |
| | | B | 11 | 19756577 | 19760576 | 19853232 | 19857231 |
| 21 | 3_9052040_9055750_9145628_9152005_FF | A | 3 | 9055719 | 9055748 | 9151974 | 9152003 |
| | | B | 3 | 9051749 | 9055748 | 9148004 | 9152003 |
| 22 | 10_106933024_106936409_106987230_106996578_RF | A | 10 | 106933026 | 106933055 | 106996547 | 106996576 |
| | | B | 10 | 106933026 | 106937025 | 106992577 | 106996576 |
| 23 | 7_43323285_43325660_43374545_43378939_RF | A | 7 | 43323287 | 43323316 | 43378908 | 43378937 |
| | | B | 7 | 43323287 | 43327286 | 43374938 | 43378937 |
| 24 | 10_14270092_14271521_14310504_14315691_RR | A | 10 | 14270094 | 14270123 | 14310506 | 14310535 |
| | | B | 10 | 14270094 | 14274093 | 14310506 | 14314505 |
| 25 | 11_131897458_131901394_132113295_132119935_RF | A | 11 | 131897460 | 131897489 | 132119904 | 132119933 |
| | | B | 11 | 131897460 | 131901459 | 132115934 | 132119933 |
| 26 | 1_245925794_245932816_246050109_246051986_RF | A | 1 | 245925796 | 245925825 | 246051955 | 246051984 |
| | | B | 1 | 245925796 | 245929795 | 246047985 | 246051984 |
| 27 | 19_31044705_31050072_31187328_31194064_FF | A | 19 | 31050041 | 31050070 | 31194033 | 31194062 |
| | | B | 19 | 31046071 | 31050070 | 31190063 | 31194062 |
| 28 | 3_61569723_61575531_61586995_61590998_RR | A | 3 | 61569725 | 61569754 | 61586997 | 61587026 |
| | | B | 3 | 61569725 | 61573724 | 61586997 | 61590996 |
| 29 | 8_3184876_3186946_3453654_3461617_FF | A | 8 | 3186915 | 3186944 | 3461586 | 3461615 |
| | | B | 8 | 3182945 | 3186944 | 3457616 | 3461615 |
| 30 | 10_106933024_106936409_106987230_106996578_FF | A | 10 | 106936378 | 106936407 | 106996547 | 106996576 |
| | | B | 10 | 106932408 | 106936407 | 106992577 | 106996576 |
| 31 | 1_34220544_34225147_34243895_34245282_RF | A | 1 | 34220546 | 34220575 | 34245251 | 34245280 |
| | | B | 1 | 34220546 | 34224545 | 34241281 | 34245280 |
| 32 | 10_114794603_114795614_114845287_114849773_RF | A | 10 | 114794605 | 114794634 | 114849742 | 114849771 |
| | | B | 10 | 114794605 | 114798604 | 114845772 | 114849771 |
| 33 | 7_127697921_127702958_127735833_127739039_RR | A | 7 | 127697923 | 127697952 | 127735835 | 127735864 |
| | | B | 7 | 127697923 | 127701922 | 127735835 | 127739834 |
| 34 | 7_147215122_147220305_147434056_147437943_FF | A | 7 | 147220274 | 147220303 | 147437912 | 147437941 |
| | | B | 7 | 147216304 | 147220303 | 147433942 | 147437941 |
| 35 | 1_7342266_7346982_7438998_7443753_RR | A | 1 | 7342268 | 7342297 | 7439000 | 7439029 |
| | | B | 1 | 7342268 | 7346267 | 7439000 | 7442999 |
| 36 | 10_335551_340193_459009_460534_RR | A | 10 | 335553 | 335582 | 459011 | 459040 |
| | | B | 10 | 335553 | 339552 | 459011 | 463010 |
| 37 | 7_43192949_43199499_43374545_43378939_RF | A | 7 | 43192951 | 43192980 | 43378908 | 43378937 |
| | | B | 7 | 43192951 | 43196950 | 43374938 | 43378937 |
| 38 | 7_29270176_29273092_29512240_29519656_RR | A | 7 | 29270178 | 29270207 | 29512242 | 29512271 |
| | | B | 7 | 29270178 | 29274177 | 29512242 | 29516241 |
| 39 | 2_236412787_236415814_236461763_236466325_FF | A | 2 | 236415783 | 236415812 | 236466294 | 236466323 |
| | | B | 2 | 236411813 | 236415812 | 236462324 | 236466323 |

TABLE 2b-continued

Probe Name, location (A) and 4 kb associated region (B).

| Seq ID* | Table 2b. Probe name | | Chr | Start1 | End1 | Start2 | End2 |
|---|---|---|---|---|---|---|---|
| 40 | 15_30011706_30019313_30190315_30193234_RF | A | 15 | 30011708 | 30011737 | 30193203 | 30193232 |
|  |  | B | 15 | 30011708 | 30015707 | 30189233 | 30193232 |
| 41 | 9_8858395_8866587_8895563_8897215_FR | A | 9 | 8866556 | 8866585 | 8895565 | 8895594 |
|  |  | B | 9 | 8862586 | 8866585 | 8895565 | 8899564 |
| 42 | 6_111982743_111987540_112042041_112045568_RR | A | 6 | 111982745 | 111982774 | 112042043 | 112042072 |
|  |  | B | 6 | 111982745 | 111986744 | 112042043 | 112046042 |

*SeqID refers to associated 60-mer Probe Sequence in Table 2a

TABLE 3

| Table 3. Probe | Seq ID* | Primer Pair | Q-value | Prev |
|---|---|---|---|---|
| 8_31516198_31523606_31818711_31822095_RR | 1 | OBD140_001/003 | 0.00443067 | AD-P |
| 8_18627026_18630239_18802479_18805120_RR | 2 | OBD140_129/131 | 0.022874494 | AD-P |
| 8_141055883_141058992_141086377_141087725_RR | 3 | OBD140_185/187 | 0.003889238 | AD-N |
| 12_99829998_99832967_99923655_99925739_FR | 4 | OBD140_261/263 | 0.006062414 | AD-N |
| 3_134760993_134763662_134867764_134877240_RR | 5 | OBD140_341/343 | 0.003889238 | AD-P |
| 9_133594848_133596271_133727385_133729777_FF | 6 | OBD140_369/371 | 0.003967781 | AD-P |
| 3_131505858_131513308_131747714_131750544_RF | 7 | OBD140_381/383 | 0.005502585 | AD-N |
| 12_13876814_13882582_14175710_14178153_FR | 8 | OBD140_397/399 | 0.00443067 | AD-P |
| 8_18627026_18630239_18683324_18685195_RR | 9 | OBD140_449/451 | 0.00961399 | AD-P |
| 8_100791664_100796954_100828549_100846158_FF | 10 | OBD140_453/455 | 0.005318479 | AD-P |
| 8_18627026_18630239_18789667_18794069_RR | 11 | OBD140_501/503 | 0.019327283 | AD-P |
| 11_83262014_83266402_83456642_83461359_FF | 12 | OBD140_557/559 | 0.00443067 | AD-P |
| 15_88561155_88565981_88737279_88740659_FR | 13 | OBD140_609/611 | 0.004284463 | AD-N |
| 8_3184876_3186946_3214817_3221560_FR | 14 | OBD140_005/007 | 0.005343515 | AD-N |
| 7_111502152_111504459_111764240_111773350_FR | 15 | OBD140_009/011 | 0.00474473 | AD-N |
| 8_3161496_3163915_3184876_3186946_RF | 16 | OBD140_013/015 | 0.004071443 | AD-N |
| 5_136390820_136396782_136690182_136694747_FR | 17 | OBD140_033/035 | 0.004071443 | AD-N |
| 5_136613132_136616425_136690182_136694747_RR | 18 | OBD140_037/039 | 0.003889238 | AD-N |
| 8_31516198_31523606_31643705_31652690_RR | 19 | OBD140_017/019 | 0.003889238 | AD-P |
| 11_19756575_19766996_19853230_19857899_RR | 20 | OBD140_045/047 | 0.014168919 | AD-N |
| 3_9052040_9055750_9145628_9152005_FF | 21 | OBD140_049/051 | 0.00443067 | AD-N |
| 10_106933024_106936409_106987230_106996578_RF | 22 | OBD140_053/055 | 0.003889238 | AD-N |
| 7_43323285_43325660_43374545_43378939_RF | 23 | OBD140_057/059 | 0.003889238 | AD-N |
| 10_14270092_14271521_14310504_14315691_RR | 24 | OBD140_061/063 | 0.006191144 | AD-P |
| 11_131897458_131901394_132113295_132119935_RF | 25 | OBD140_069/071 | 0.004284463 | AD-N |
| 1_245925794_245932816_246050109_246051986_RF | 26 | OBD140_073/075 | 0.007163017 | AD-N |
| 19_31044705_31050072_31187328_31194064_FF | 27 | OBD140_081/083 | 0.003889238 | AD-N |
| 3_61569723_61575531_61586995_61590998_RR | 28 | OBD140_085/087 | 0.003889238 | AD-N |
| 8_3184876_3186946_3453654_3461617_FF | 29 | OBD140_089/091 | 0.003889238 | AD-N |
| 10_106933024_106936409_106987230_106996578_FF | 30 | OBD140_101/103 | 0.004647778 | AD-P |
| 1_34220544_34225147_34243895_34245282_RF | 31 | OBD140_133/135 | 0.00388924 | AD-P |
| 10_114794603_114795614_114845287_114849773_RF | 32 | OBD140_177/179 | 0.00388924 | AD-N |
| 7_127697921_127702958_127735833_127739039_RR | 33 | OBD140_213/215 | 0.00485586 | AD-N |
| 7_147215122_147220305_147434056_147437943_FF | 34 | OBD140_229/231 | 0.00388924 | AD-N |
| 1_7342266_7346982_7438998_7443753_RR | 35 | OBD140_265/267 | 0.00248671 | AD-N |
| 10_335551_340193_459009_460534_RR | 36 | OBD140_281/283 | 0.00388924 | AD-N |
| 7_43192949_43199499_43374545_43378939_RF | 37 | OBD140_293/295 | 0.00440647 | AD-N |
| 7_29270176_29273092_29512240_29519656_RR | 38 | OBD140_333/335 | 0.00388924 | AD-P |
| 2_236412787_236415814_236461763_236466325_FF | 39 | OBD140_393/395 | 0.00478485 | AD-N |
| 15_30011706_30019313_30190315_30193234_RF | 40 | OBD140_573/575 | 0.00574021 | AD-P |
| 9_8858395_8866587_8895563_8897215_FR | 41 | OBD140_577/579 | 0.00795778 | AD-P |
| 6_111982743_111987540_112042041_112045568_RR | 42 | OBD140_617/619 | 0.00443067 | AD-N |

*SeqID refers to associated 60-mer Probe Sequence in Table 2a

TABLE 3b

Sequence of Primers with associated SeqIDs corresponding to probes and primers pairs in Table 3a

| Primer pair | Seq ID | PCR-Primer1_ID | PCR_Primer1 | Seq Id | PCR-Primer2_ID | PCR_Primer2 |
|---|---|---|---|---|---|---|
| OBD140_001/003 | 43 | OBD140_001 | TCACTCTCCCTTCCCTCTG | 85 | OBD140_003 | GGTCTGATTATACTGATTTGGATGC |
| OBD140_129/131 | 44 | OBD140_129 | AATGCAGATTTGTGCTTGC | 86 | OBD140_131 | CAGCTAGTGTTGAGGTCTTAG |
| OBD140_185/187 | 45 | OBD140_185 | GAACCACCATTTGGTGAAAG | 87 | OBD140_187 | AGAAAGAACAGTGTCTGTGG |
| OBD140_261/263 | 46 | OBD140_261 | CCACCTCACACCATACAC | 88 | OBD140_263 | GCCTGCAAAGCCTAAATG |

TABLE 3b-continued

Sequence of Primers with associated SeqIDs corresponding to probes and primers pairs in Table 3a

| Primer pair | Seq ID | PCR-Primer1_ID | PCR_Primer1 | Seq Id | PCR-Primer2_ID | PCR_Primer2 |
|---|---|---|---|---|---|---|
| OBD140_341/343 | 47 | OBD140_341 | AAAGATGAGGCCGGGTATGG | 89 | OBD140_343 | CCCAACAGAGTACAGGCACC |
| OBD140_369/371 | 48 | OBD140_369 | GTAAGAGTGATGATGCTTGGAC | 90 | OBD140_371 | CAGGAGATAGAAATCTGGGAATTG |
| OBD140_381/383 | 49 | OBD140_381 | TGATTACACACAACACTGACG | 91 | OBD140_383 | GAAATGAACTGAAGCATGATGG |
| OBD140_397/399 | 50 | OBD140_397 | GCAGAGAATGGAGCCAAATG | 92 | OBD140_399 | GGCCATAAACTCAAACCTAGTG |
| OBD140_449/451 | 51 | OBD140_449 | GTAGATAGTGGTGGTGATTGC | 93 | OBD140_451 | CCACTCAAACGCTCATCTC |
| OBD140_453/455 | 52 | OBD140_453 | CGGAAACCCAAGAGTGTTTAG | 94 | OBD140_455 | ACACTGTAGAGGAGTGGTTATC |
| OBD140_501/503 | 53 | OBD140_501 | GAATAACTGCTGGTGGGTATG | 95 | OBD140_503 | GTATCTTGTTCCTCCCACTTTAC |
| OBD140_557/559 | 54 | OBD140_557 | AGATGAGACCAGAGGGAAG | 96 | OBD140_559 | CACTGGCCCTAGGATTTAAG |
| OBD140_609/611 | 55 | OBD140_609 | ACTGAGCGAAACAGAAAGG | 97 | OBD140_611 | AGGAGAGAGTGTAGTCAAGG |
| OBD140_005/007 | 56 | OBD140_008 | ATGACCCATTTGCAGCGTGA | 98 | OBD140_007 | GGTAGACTAGGCACTGCTTCAGG |
| OBD140_009/011 | 57 | OBD140_009 | GCTCACATCAAATCTCAAAGGGCA | 99 | OBD140_011 | GTGGCTGTAAGGACATGGGTAGAA |
| OBD140_013/015 | 58 | OBD140_013 | AGCGTGACAGAGCCCAGTTC | 100 | OBD140_015 | TTGAGGCCCAGAGCAACTTCT |
| OBD140_033/035 | 59 | OBD140_033 | TCAGCAGTTACCTCAGAGTCCT | 101 | OBD140_035 | TGCTTGGAGGCAGATACCCTC |
| OBD140_037/039 | 60 | OBD140_037 | TTGAGAGGCCCGTCATCTGT | 102 | OBD140_039 | GTGC1TGGAGGCAGATACCCT |
| OBD140_017/019 | 61 | OBD140_017 | GGTGGCTCATACCATAGCACCA | 103 | OBD140_019 | CCAACAGAGTACAGGCACCCA |
| OBD140_045/047 | 62 | OBD140_045 | GCTCACTGCCATCCTGCAAC | 104 | OBD140_047 | CAGACCCCCTTGGGGAACAT |
| OBD140_049/051 | 63 | OBD140_049 | ATTCGCTCGCCACATCTCCT | 105 | OBD140_051 | GCACCTGGGGAGTAGAAGG |
| OBD140_053/055 | 64 | OBD140_053 | GCCATGCAGTGTCTGATAGGT | 106 | OBD140_055 | GAGTGTTAAACAATTGAGGGGGA |
| OBD140_057/059 | 65 | OBD140_057 | ATTCCATTGTGTCCCTCTGTTCCT | 107 | OBD140_059 | TTTGGGGTCCCACTTTGAGGG |
| OBD140_061/063 | 66 | OBD140_061 | TTGAATTCCTGGGTGTGAGTTTTGC | 108 | OBD140_063 | AGTCCTTGGCAGGTAGGTAGC |
| OBD140_069/071 | 67 | OBD140_069 | CCAGGCACTTTCTCTCGGTTTT | 109 | OBD140_071 | GGGGAAGAGGGCTTACCAATAGAG |
| OBD140_073/075 | 68 | OBD140_073 | CCGGATTGTCCAGCGTCACT | 110 | OBD140_075 | AGAACACCGCACCGTCTGTT |
| OBD140_081/083 | 69 | OBD140_081 | CCGCAACAGGACAATTGCATCA | 111 | OBD140_083 | CGTGCTGGGTGGTGAGTAAC |
| OBD140_085/087 | 70 | OBD140_085 | CAGAGAGGCTGTCCCTAGCAC | 112 | OBD140_087 | GGCCAACATGCCCACATTCTAC |
| OBD140_089/091 | 71 | OBD140_089 | GACTCTGGACAGCCGGACC | 113 | OBD140_091 | GATCTAGCAAATGGCCAAGGCTTA |
| OBD140_101/103 | 72 | OBD140_101 | CATCAAATAAACCAGCAGACAG | 114 | OBD140_103 | CTGATGAAGGAGATGCATAGAG |
| OBD140_133/135 | 73 | OBD140_133 | GTTATTGTCGCTGCTGTTTG | 115 | OBD140_135 | TCCATCTGTGTTTCTCAAGTC |
| OBD140_177/179 | 74 | OBD140_177 | CAGTTCACAATGGAGGAGAAG | 116 | OBD140_179 | GAGATGGAAAGGGAAGGAAAG |
| OBD140_213/215 | 75 | OBD140_213 | GTCTCATTTCCACCACCTC | 117 | OBD140_215 | CATCTACTGGGATAGAAGTCAAG |
| OBD140_229/231 | 76 | OBD140_229 | GTCTCTCACAGTCAAGATGC | 118 | OBD140_231 | GTGCAAGGAATTTATGAAAGGG |
| OBD140_265/267 | 77 | OBD140_265 | AGAGAGAAGGCTGGACTTG | 119 | OBD140_267 | AAGAAGCCAGGGAGGAG |
| OBD140_281/283 | 78 | OBD140_281 | GAGACACTCAGGCTTCTTTC | 120 | OBD140_283 | TCTGTCTGCTTCAGCTTTAC |
| OBD140_293/295 | 79 | OBD140_293 | CGGTGGATCATTCCATTGT | 121 | OBD140_295 | GGGCTCTGAACTGAATGTAG |

TABLE 3b-continued

Sequence of Primers with associated SeqIDs corresponding to probes and primers pairs in Table 3a

| Primer pair | Seq ID | PCR-Primer1_ID | PCR_Primer1 | Seq Id | PCR-Primer2_ID | PCR_Primer2 |
|---|---|---|---|---|---|---|
| OBD140_333/335 | 80 | OBD140_333 | ACAGGGATGGATATTTGGTGGAG | 122 | OBD140_335 | GCCCACTGACACAAAGACTC |
| OBD140_393/395 | 81 | OBD140_393 | CAGGACTTGAGCTTGGAGGG | 123 | OBD140_395 | CTGTGCCAATAACTCTCAGTGC |
| OBD140_573/575 | 82 | OBD140_573 | GCAGCCACAGAAATGAGTAG | 124 | OBD140_575 | TCGCATGTAGATCCAACAAAG |
| OBD140_577/579 | 83 | OBD140_577 | ACGTGCTGCCCAATTAAC | 125 | OBD140_579 | TCAAGTGTGACATGCTGAAG |
| OBD140_617/619 | 84 | OBD140_617 | TAGCTTTCAATTCCGTAGCC | 126 | OBD140_619 | CACTGGTGGTCCCATTTAC |

TABLE 4

| Probe | Prev | Locus | Full Name/Alias |
|---|---|---|---|
| 12_13876814_13882582_14175710_14178153_FR | AD-P | GRIN2B | Glutamate Ionotropic Receptor NMDA Type Subunit 2B |
| 8_31516198_31523606_31818711_31822095_RR | AD-P | NRG1 | Neuregulin 1 |
| 8_31516198_31523606_31643705_31652690_RR | AD-P | NRG1 | Neuregulin 1 |
| 3_134760993_134763662_134867764_134877240_RR | AD-P | EPHB1 | EPH Receptor B1 |
| 8_18627026_18630239_18802479_18805120_RR | AD-P | PSD3 | Pleckstrin And Sec7 Domain Containing 3 |
| 10_14270092_14271521_14310504_14315691_RR | AD-P | FRMD4A | FERM Domain Containing 4A |
| 9_133594848_133596271_133727385_133729777_FF | AD-P | ABL1 | ABL Proto-Oncogene 1, Non-Receptor Tyrosine Kinase |
| 11_19756575_19766996_19853230_19857899_RR | AD-N | NAV2 | Neuron Navigator 2 |
| 3_9052040_9055750_9145628_9152005_FF | AD-N | SRGAP3 | SLIT-ROBO Rho GTPase Activating Protein 3 |
| 7_111502152_111504459_111764240_111773350_FR | AD-N | DOCK4 | Dedicator Of Cytokinesis 4 |
| 10_106933024_106936409_106987230_106996578_RF | AD-N | SORCS3 | Sortilin Related VPS10 Domain Containing Receptor 3 |
| 8_3184876_3186946_3453654_3461617_FF | AD-N | CSMD1 | CUB And Sushi Multiple Domains 1 |
| 7_43323285_43325660_43374545_43378939_RF | AD-N | HECW1 | HECT, C2 And WW Domain Containing E3 Ubiquitin Protein Ligase 1 |
| 8_3161496_3163915_3184876_3186946_RF | AD-N | CSDM1 | CUB And Sushi Multiple Domains 1 |

---

The invention claimed is:

1. A method of identifying a human individual in need of therapy for Alzheimer's disease and treating the identified human individual, the method comprising:
   (A) assaying a blood sample from a human individual for ten chromosome interactions, wherein said assaying comprises the steps of:
      (a) performing in vitro cross-linking of chromosome regions of the human individual which have come together in a chromosome interaction to form cross-linked nucleic acid;
      (b) subjecting said cross-linked nucleic acid to restriction digestion cleavage with an enzyme to form cross-linked cleaved nucleic acids;
      (c) ligating said cross-linked cleaved nucleic acid ends to form a ligated nucleic acid; and
      (d) detecting the ligated nucleic acid to determine the presence or absence of a chromosome interaction and wherein the ten chromosome interactions are the following chromosomal interactions:
         (i) the chromosome interaction on chromosome 12 that results in a ligated nucleic acid comprising SEQ ID NO: 8;
         (ii) the chromosome interaction on chromosome 8 that results in a ligated nucleic acid comprising SEQ ID NO: 1;
         (iii) the chromosome interaction on chromosome 8 that results in a ligated nucleic acid comprising SEQ ID NO: 19;
         (iv) the chromosome interaction on chromosome 3 that results in a ligated nucleic acid comprising SEQ ID NO: 5;
         (v) the chromosome interaction on chromosome 8 that results in a ligated nucleic acid comprising SEQ ID NO: 2;
         (vi) the chromosome interaction on chromosome 10 that results in a ligated nucleic acid comprising SEQ ID NO: 24;
         (vii) the chromosome interaction on chromosome 9 that results in a ligated nucleic acid comprising SEQ ID NO: 6;
         (viii) the chromosome interaction on chromosome 11 that results in a ligated nucleic acid comprising SEQ ID NO:20;
         (ix) the chromosome interaction on chromosome 3 that results in a ligated nucleic acid comprising SEQ ID NO:21; and
         (x) the chromosome interaction on chromosome 7 that results in a ligated nucleic acid comprising SEQ ID NO:15;
   (B) identifying the human individual as being in need of therapy for Alzheimer's disease when one or more of chromosome interactions (i)-(vii) are present and/or one or more of chromosome interactions (viii)-(x) are absent; and
   (C) administering to the identified human individual an agent that is therapeutic for Alzheimer's disease.

* * * * *